(12) United States Patent
Mueller et al.

(10) Patent No.: US 7,918,876 B2
(45) Date of Patent: Apr. 5, 2011

(54) SPINAL IMPLANT ADJUSTMENT DEVICE

(75) Inventors: Richard Mueller, Macedonia, OH (US);
Andrew Budd, Uniontown, OH (US);
Marc Silski, Hartville, OH (US)

(73) Assignee: Theken Spine, LLC, Akron, OH (US)

( * ) Notice: Subject to any disclaimer, the term of this patent is extended or adjusted under 35 U.S.C. 154(b) by 1499 days.

(21) Appl. No.: 10/550,329

(22) PCT Filed: Mar. 24, 2004

(86) PCT No.: PCT/US2004/008980
§ 371 (c)(1),
(2), (4) Date: Sep. 22, 2005

(87) PCT Pub. No.: WO2004/084742
PCT Pub. Date: Oct. 7, 2004

(65) Prior Publication Data
US 2006/0217712 A1    Sep. 28, 2006

(51) Int. Cl.
*A61B 17/70* (2006.01)

(52) U.S. Cl. ........ 606/251; 606/250; 606/276; 606/277; 606/288

(58) Field of Classification Search .................. 606/250, 606/251, 258, 259, 105; 403/43–48, 204, 403/343, 370, 370.3; 623/17.15
See application file for complete search history.

(56) References Cited

U.S. PATENT DOCUMENTS

| | | | |
|---|---|---|---|
| 2,677,369 A | 5/1954 | Knowles | |
| 3,307,505 A | 3/1967 | Windross | |
| 3,745,995 A | 7/1973 | Kraus | |
| 3,774,244 A | 11/1973 | Walker | |
| 3,837,753 A * | 9/1974 | Weiste et al. | 403/33 |
| 3,848,601 A | 11/1974 | Ma et al. | |
| 3,855,638 A | 12/1974 | Pilliar | |
| 3,867,728 A | 2/1975 | Stubstad et al. | |
| 3,894,467 A | 7/1975 | Brescia | |
| 3,906,550 A | 9/1975 | Rostoker et al. | |
| 4,026,304 A | 5/1977 | Levy | |
| 4,126,057 A * | 11/1978 | von Allworden et al. | 74/586 |
| 4,285,071 A | 8/1981 | Nelson et al. | |
| 4,309,777 A | 1/1982 | Patil | |

(Continued)

FOREIGN PATENT DOCUMENTS

CA    2088066    1/1992

(Continued)

*Primary Examiner* — Thomas C Barrett
*Assistant Examiner* — Andrew Yang
(74) *Attorney, Agent, or Firm* — Middleton Reutlinger; Robert H. Eichenberger; Eric L. Killmeier

(57) ABSTRACT

An adjustable spinal implant (10) is provided for use in connecting elongate members (12) as well as vertebral spacers such as corpectomy devices, intervertebral fusion devices, and other prostheses. The implant (10) may have fittings (80) on either end comprising fixed (100) or articulating (200) jaws, endplates, or other engagement structures. The implant (10) comprises a housing (40) with an internal rotor (60); an extending shaft (20); and a locking collar (70). The extending shaft (20) has an external helical groove (23) that meshes with an internal helical groove (63) on rotor (20). Length adjustment occurs by transforming axial movement of the extending shaft (20) into a rotary movement of the rotor (60) via helical engagement. The locking collar (70) comprises protrusion (73) engaging grooves (63) of rotor (60), thus providing a simple, positive locking mechanism without requiring the surgeon to apply excessive force to lock the length.

58 Claims, 25 Drawing Sheets

U.S. PATENT DOCUMENTS

| | | |
|---|---|---|
| 4,349,921 A | 9/1982 | Kuntz |
| 4,361,141 A | 11/1982 | Tanner |
| 4,429,691 A | 2/1984 | Niwa et al. |
| 4,484,570 A | 11/1984 | Sutter et al. |
| 4,501,269 A | 2/1985 | Bagby |
| 4,542,539 A | 9/1985 | Rowe, Jr. et al. |
| 4,553,273 A | 11/1985 | Wu |
| 4,554,914 A | 11/1985 | Kapp et al. |
| 4,563,778 A | 1/1986 | Roche et al. |
| 4,567,884 A | 2/1986 | Edwards |
| 4,611,582 A | 9/1986 | Duff |
| 4,648,388 A | 3/1987 | Steffee |
| 4,657,550 A | 4/1987 | Daher |
| 4,693,721 A | 9/1987 | Ducheyne |
| 4,714,469 A | 12/1987 | Kenna |
| 4,736,738 A | 4/1988 | Lipovsek et al. |
| 4,743,256 A | 5/1988 | Brantigan |
| 4,759,766 A | 7/1988 | Buettner-Janz et al. |
| 4,781,591 A | 11/1988 | Allen |
| 4,815,453 A | 3/1989 | Cotrel |
| 4,820,305 A | 4/1989 | Harms et al. |
| 4,834,757 A | 5/1989 | Brantigan |
| 4,877,020 A | 10/1989 | Vich |
| 4,878,915 A | 11/1989 | Brantigan |
| 4,892,546 A | 1/1990 | Kotz et al. |
| 4,932,975 A | 6/1990 | Main et al. |
| 4,938,768 A | 7/1990 | Wu |
| 4,946,378 A | 8/1990 | Hirayama et al. |
| 4,961,740 A | 10/1990 | Ray et al. |
| 5,005,562 A | 4/1991 | Cotrel |
| 5,010,879 A | 4/1991 | Moriya et al. |
| 5,024,213 A | 6/1991 | Asher et al. |
| 5,026,373 A | 6/1991 | Ray et al. |
| 5,055,104 A | 10/1991 | Ray |
| 5,062,845 A | 11/1991 | Kuslich et al. |
| 5,071,437 A | 12/1991 | Steffee |
| 5,084,049 A | 1/1992 | Asher et al. |
| 5,092,893 A | 3/1992 | Smith |
| 5,102,412 A | 4/1992 | Rogozinski |
| 5,116,334 A | 5/1992 | Cozad et al. |
| 5,133,716 A | 7/1992 | Plaza |
| 5,133,717 A | 7/1992 | Chopin |
| 5,147,359 A | 9/1992 | Cozad et al. |
| 5,147,360 A | 9/1992 | Dubousset |
| 5,147,402 A | 9/1992 | Bohler et al. |
| 5,154,718 A | 10/1992 | Cozad et al. |
| 5,171,278 A | 12/1992 | Pisharodi |
| 5,171,281 A | 12/1992 | Parsons et al. |
| 5,181,917 A | 1/1993 | Rogozinski |
| 5,192,326 A | 3/1993 | Bao et al. |
| 5,192,327 A | 3/1993 | Brantigan |
| 5,201,766 A | 4/1993 | Georgette |
| 5,222,983 A | 6/1993 | Schmitz et al. |
| 5,236,460 A | 8/1993 | Barber |
| 5,250,061 A | 10/1993 | Michelson |
| 5,261,907 A | 11/1993 | Vignaud et al. |
| 5,275,600 A | 1/1994 | Allard et al. |
| 5,282,801 A | 2/1994 | Sherman |
| 5,290,312 A | 3/1994 | Kojimoto et al. |
| 5,290,494 A | 3/1994 | Coombes et al. |
| 5,300,076 A | 4/1994 | Leriche |
| 5,304,210 A | 4/1994 | Crook |
| 5,306,307 A | 4/1994 | Senter et al. |
| 5,306,309 A | 4/1994 | Wagner et al. |
| 5,312,405 A | 5/1994 | Korotko et al. |
| 5,314,478 A | 5/1994 | Oka et al. |
| 5,330,473 A | 7/1994 | Howland |
| 5,330,535 A | 7/1994 | Moser et al. |
| 5,334,203 A | 8/1994 | Wagner |
| 5,336,223 A | 8/1994 | Rogers |
| 5,352,224 A | 10/1994 | Westermann |
| 5,364,400 A | 11/1994 | Rego, Jr. et al. |
| 5,368,594 A | 11/1994 | Martin et al. |
| 5,387,212 A | 2/1995 | Yuan et al. |
| 5,390,683 A | 2/1995 | Pisharodi |
| 5,395,370 A | 3/1995 | Muller et al. |
| 5,395,372 A | 3/1995 | Holt et al. |
| 5,397,363 A | 3/1995 | Gelbard |
| 5,397,364 A | 3/1995 | Kozak et al. |
| 5,403,316 A | 4/1995 | Ashman |
| 5,405,391 A | 4/1995 | Henderson et al. |
| 5,413,602 A | 5/1995 | Metz-Stavenhagen |
| 5,423,818 A | 6/1995 | Van Hoeck et al. |
| 5,425,772 A | 6/1995 | Brantigan |
| 5,431,658 A | 7/1995 | Moskovich |
| 5,437,671 A | 8/1995 | Lozier et al. |
| 5,439,463 A | 8/1995 | Lin |
| 5,443,514 A | 8/1995 | Steffee |
| 5,443,515 A | 8/1995 | Cohen et al. |
| 5,445,639 A | 8/1995 | Kuslich et al. |
| 5,454,811 A | 10/1995 | Huebner |
| 5,454,812 A | 10/1995 | Lin |
| 5,458,638 A | 10/1995 | Kuslich et al. |
| 5,458,643 A | 10/1995 | Oka et al. |
| 5,474,551 A | 12/1995 | Finn et al. |
| 5,476,462 A | 12/1995 | Allard et al. |
| 5,487,742 A | 1/1996 | Cotrel |
| 5,489,308 A | 2/1996 | Kuslich et al. |
| 5,498,263 A | 3/1996 | DiNello et al. |
| 5,514,132 A | 5/1996 | Csernatony et al. |
| 5,514,180 A | 5/1996 | Heggeness et al. |
| 5,522,879 A | 6/1996 | Scopelianos |
| 5,522,899 A | 6/1996 | Michelson |
| 5,524,624 A | 6/1996 | Tepper et al. |
| 5,534,030 A | 7/1996 | Navarro et al. |
| 5,545,229 A | 8/1996 | Parsons et al. |
| 5,549,679 A | 8/1996 | Kuslich |
| 5,562,736 A | 10/1996 | Ray et al. |
| 5,562,738 A | 10/1996 | Boyd et al. |
| 5,565,005 A | 10/1996 | Erickson et al. |
| 5,571,190 A | 11/1996 | Ulrich et al. |
| 5,571,192 A | 11/1996 | Schonhoffer |
| 5,582,612 A | 12/1996 | Lin |
| 5,586,983 A | 12/1996 | Sanders et al. |
| 5,593,409 A | 1/1997 | Michelson |
| 5,601,552 A | 2/1997 | Cotrel |
| 5,607,424 A | 3/1997 | Tropiano |
| 5,609,593 A | 3/1997 | Errico et al. |
| 5,609,594 A | 3/1997 | Errico et al. |
| 5,609,635 A | 3/1997 | Michelson |
| 5,609,636 A | 3/1997 | Kohrs et al. |
| 5,609,637 A | 3/1997 | Biedermann et al. |
| 5,611,800 A | 3/1997 | Davis et al. |
| 5,615,965 A | 4/1997 | Saurat et al. |
| 5,620,444 A | 4/1997 | Assaker |
| 5,624,442 A | 4/1997 | Mellinger et al. |
| 5,630,816 A | 5/1997 | Kambin |
| 5,645,598 A | 7/1997 | Brosnahan, III |
| 5,651,789 A | 7/1997 | Cotrel |
| 5,653,761 A | 8/1997 | Pisharodi |
| 5,653,762 A | 8/1997 | Pisharodi |
| 5,658,336 A | 8/1997 | Pisharodi |
| 5,658,337 A | 8/1997 | Kohrs et al. |
| 5,665,089 A | 9/1997 | Dall et al. |
| 5,665,119 A | 9/1997 | Koller |
| 5,665,122 A | 9/1997 | Kambin |
| 5,667,506 A | 9/1997 | Sutterlin |
| 5,667,507 A | 9/1997 | Corin et al. |
| 5,669,909 A | 9/1997 | Zdeblick et al. |
| 5,669,910 A | 9/1997 | Korhonen et al. |
| 5,674,294 A | 10/1997 | Bainville et al. |
| 5,676,665 A | 10/1997 | Bryan |
| 5,681,312 A | 10/1997 | Yuan et al. |
| 5,683,393 A | 11/1997 | Ralph |
| 5,683,394 A | 11/1997 | Rinner |
| 5,683,464 A | 11/1997 | Wagner et al. |
| 5,700,264 A | 12/1997 | Zucherman et al. |
| 5,700,291 A | 12/1997 | Kuslich et al. |
| 5,702,449 A | 12/1997 | McKay |
| 5,702,451 A | 12/1997 | Biedermann et al. |
| 5,702,453 A | 12/1997 | Rabbe et al. |
| 5,702,455 A | 12/1997 | Saggar |
| 5,707,372 A | 1/1998 | Errico et al. |
| 5,709,684 A | 1/1998 | Errico et al. |
| 5,709,685 A | 1/1998 | Dombrowski et al. |
| 5,711,957 A | 1/1998 | Patat et al. |
| 5,713,900 A | 2/1998 | Benzel et al. |

| | | | | | | |
|---|---|---|---|---|---|---|
| 5,716,355 | A | 2/1998 | Jackson et al. | 6,102,950 | A | 8/2000 | Vaccaro |
| 5,716,415 | A | 2/1998 | Steffee | 6,106,557 | A | 8/2000 | Robioneck et al. |
| 5,723,013 | A | 3/1998 | Jeanson et al. | 6,113,600 | A | 9/2000 | Drummond et al. |
| 5,743,907 | A | 4/1998 | Asher et al. | 6,113,638 | A | 9/2000 | Williams et al. |
| 5,743,911 | A | 4/1998 | Cotrel | 6,120,503 | A | 9/2000 | Michelson |
| 5,749,916 | A | 5/1998 | Richelsoph | 6,120,506 | A | 9/2000 | Kohrs et al. |
| 5,752,955 | A | 5/1998 | Errico | 6,123,705 | A | 9/2000 | Michelson |
| 5,766,176 | A | 6/1998 | Duncan | 6,126,660 | A | 10/2000 | Dietz |
| 5,766,252 | A | 6/1998 | Henry et al. | 6,136,003 | A | 10/2000 | Hoeck et al. |
| 5,766,253 | A | 6/1998 | Brosnahan, III | 6,136,031 | A | 10/2000 | Middleton |
| 5,772,661 | A | 6/1998 | Michelson | 6,139,548 | A | 10/2000 | Errico |
| 5,776,196 | A | 7/1998 | Matsuzaki et al. | 6,143,032 | A | 11/2000 | Schafer et al. |
| 5,776,197 | A | 7/1998 | Rabbe et al. | 6,143,033 | A | 11/2000 | Paul et al. |
| 5,776,198 | A | 7/1998 | Rabbe et al. | 6,149,651 | A | 11/2000 | Drewry et al. |
| 5,776,199 | A | 7/1998 | Michelson | 6,159,211 | A | 12/2000 | Boriani et al. |
| 5,782,830 | A | 7/1998 | Farris | 6,159,244 | A | 12/2000 | Suddaby |
| 5,782,832 | A | 7/1998 | Larsen et al. | 6,171,311 | B1 | 1/2001 | Richelsoph |
| 5,782,919 | A | 7/1998 | Zdeblick et al. | 6,174,311 | B1 | 1/2001 | Branch et al. |
| 5,785,710 | A | 7/1998 | Michelson | 6,174,334 | B1 | 1/2001 | Suddaby |
| 5,797,909 | A | 8/1998 | Michelson | 6,176,881 | B1 | 1/2001 | Schar et al. |
| 5,800,547 | A | 9/1998 | Schafer et al. | 6,176,882 | B1 | 1/2001 | Biedermann et al. |
| 5,800,549 | A | 9/1998 | Bao et al. | 6,190,413 | B1 | 2/2001 | Sutcliffe |
| 5,800,550 | A | 9/1998 | Sertich | 6,193,755 | B1 | 2/2001 | Metz-Stevenhagen et al. |
| 5,810,818 | A | 9/1998 | Errico et al. | 6,193,756 | B1 | 2/2001 | Studer et al. |
| 5,814,048 | A | 9/1998 | Morgan | 6,200,348 | B1 | 3/2001 | Biedermann et al. |
| 5,814,084 | A | 9/1998 | Grivas et al. | 6,206,924 | B1 | 3/2001 | Timm |
| D403,069 | S | 12/1998 | Drewry et al. | 6,217,578 | B1 | 4/2001 | Crozet et al. |
| 5,865,845 | A | 2/1999 | Thalgott | 6,224,595 | B1 | 5/2001 | Michelson |
| 5,865,848 | A | 2/1999 | Baker | 6,234,705 | B1 | 5/2001 | Troxell |
| 5,885,284 | A | 3/1999 | Errico et al. | 6,238,396 | B1 | 5/2001 | Lombardo |
| 5,885,299 | A | 3/1999 | Winslow et al. | 6,238,397 | B1 | 5/2001 | Zucherman et al. |
| 5,888,222 | A | 3/1999 | Coates et al. | 6,241,729 | B1 | 6/2001 | Estes et al. |
| 5,888,224 | A | 3/1999 | Beckers et al. | 6,245,072 | B1 | 6/2001 | Zdeblick et al. |
| 5,888,227 | A | 3/1999 | Cottle | 6,245,108 | B1 | 6/2001 | Biscup |
| 5,893,890 | A | 4/1999 | Pisharodi | 6,248,104 | B1 | 6/2001 | Chopin et al. |
| 5,897,556 | A | 4/1999 | Drewry et al. | 6,254,603 | B1 | 7/2001 | Gertzbein et al. |
| 5,899,903 | A | 5/1999 | Cotrel | 6,258,125 | B1 | 7/2001 | Paul et al. |
| 5,904,719 | A | 5/1999 | Errico et al. | 6,283,967 | B1 | 9/2001 | Troxell et al. |
| 5,910,315 | A | 6/1999 | Stevenson et al. | 6,290,724 | B1 | 9/2001 | Marino |
| 5,913,860 | A | 6/1999 | Scholl | 6,296,665 | B1 | 10/2001 | Strnad et al. |
| 5,928,231 | A | 7/1999 | Klein et al. | 6,302,882 | B1 | 10/2001 | Lin et al. |
| 5,928,232 | A | 7/1999 | Howland et al. | 6,306,137 | B2 | 10/2001 | Troxell |
| 5,944,720 | A | 8/1999 | Lipton | D450,121 | S | 11/2001 | Anderson |
| 5,947,966 | A | 9/1999 | Drewry et al. | 6,315,797 | B1 | 11/2001 | Middleton |
| 5,951,556 | A | 9/1999 | Faccioli et al. | 6,325,827 | B1 | 12/2001 | Lin |
| 5,957,836 | A | 9/1999 | Johnson | 6,328,740 | B1 | 12/2001 | Richelsoph |
| 5,961,554 | A | 10/1999 | Janson et al. | 6,328,741 | B1 | 12/2001 | Richelsoph |
| 5,968,062 | A | 10/1999 | Thomas et al. | 6,332,895 | B1 | 12/2001 | Suddaby |
| 5,968,098 | A | 10/1999 | Winslow | 6,344,057 | B1 | 2/2002 | Rabbe et al. |
| 5,972,031 | A | 10/1999 | Biedermann et al. | 6,371,988 | B1 | 4/2002 | Pafford et al. |
| 5,976,135 | A | 11/1999 | Sherman et al. | 6,375,681 | B1 | 4/2002 | Truscott |
| 5,980,523 | A | 11/1999 | Jackson | 6,387,097 | B1 | 5/2002 | Alby |
| 5,980,540 | A | 11/1999 | Bruce | 6,395,034 | B1 | 5/2002 | Suddaby |
| 5,989,251 | A | 11/1999 | Nichols | 6,395,035 | B2 | 5/2002 | Bresina et al. |
| 5,989,289 | A | 11/1999 | Coates et al. | 6,402,749 | B1 | 6/2002 | Ashman |
| 5,989,290 | A | 11/1999 | Biedermann et al. | 6,402,751 | B1 | 6/2002 | Hoeck |
| 6,004,326 | A | 12/1999 | Castro et al. | 6,409,765 | B1 | 6/2002 | Bianchi et al. |
| 6,015,436 | A | 1/2000 | Schonhoffer | 6,413,258 | B1 | 7/2002 | Bernhardt, Jr. |
| 6,019,793 | A | 2/2000 | Perren et al. | 6,425,920 | B1 | 7/2002 | Hamada |
| 6,033,405 | A | 3/2000 | Winslow et al. | 6,428,544 | B1 | 8/2002 | Ralph et al. |
| 6,039,762 | A | 3/2000 | McKay | 6,432,108 | B1 | 8/2002 | Burgess et al. |
| 6,045,579 | A | 4/2000 | Hochshuler et al. | 6,436,101 | B1 | 8/2002 | Hamada |
| 6,059,829 | A | 5/2000 | Schlapfer et al. | 6,440,142 | B1 | 8/2002 | Ralph et al. |
| 6,063,088 | A | 5/2000 | Winslow | 6,443,987 | B1 | 9/2002 | Bryan |
| 6,066,175 | A | 5/2000 | Henderson et al. | 6,454,805 | B1 | 9/2002 | Baccelli et al. |
| 6,074,423 | A | 6/2000 | Lawson | 6,454,806 | B1 | 9/2002 | Cohen et al. |
| 6,077,263 | A | 6/2000 | Ameil et al. | 6,458,159 | B1 | 10/2002 | Thalgott |
| 6,080,155 | A | 6/2000 | Michelson | 6,468,311 | B2 | 10/2002 | Boyd et al. |
| 6,080,193 | A | 6/2000 | Hochshuler et al. | 6,471,704 | B2 | 10/2002 | Gertzbein |
| 6,083,225 | A | 7/2000 | Winslow et al. | 6,471,724 | B2 | 10/2002 | Zdeblick et al. |
| 6,083,226 | A | 7/2000 | Fiz | 6,471,958 | B2 | 10/2002 | Dimitrijevich et al. |
| 6,086,613 | A | 7/2000 | Camino et al. | 6,475,218 | B2 | 11/2002 | Gournay et al. |
| 6,090,143 | A | 7/2000 | Meriwether et al. | 6,478,801 | B1 | 11/2002 | Ralph et al. |
| 6,093,205 | A | 7/2000 | McLeod et al. | 6,478,823 | B1 | 11/2002 | Michelson |
| 6,093,207 | A | 7/2000 | Pisharodi | 6,494,883 | B1 | 12/2002 | Ferree |
| 6,096,038 | A | 8/2000 | Michelson | 6,500,205 | B1 | 12/2002 | Michelson |
| 6,096,039 | A | 8/2000 | Stoltenberg | 6,500,206 | B1 | 12/2002 | Bryan |
| 6,099,483 | A | 8/2000 | Palmer et al. | 6,520,996 | B1 | 2/2003 | Manasas et al. |
| 6,102,948 | A | 8/2000 | Brosnahan, III | 6,524,310 | B1 | 2/2003 | Lombardo et al. |

| | | | | | | |
|---|---|---|---|---|---|---|
| 6,524,315 B1 | 2/2003 | Selvitelli et al. | | 6,855,167 B2 | 2/2005 | Shimp et al. |
| 6,524,318 B1 | 2/2003 | Longhini et al. | | 6,855,168 B2 | 2/2005 | Crozet |
| 6,524,341 B2 | 2/2003 | Lang et al. | | 6,863,673 B2 | 3/2005 | Gerbec et al. |
| 6,537,320 B1 | 3/2003 | Michelson | | 6,863,689 B2 | 3/2005 | Ralph et al. |
| 6,544,265 B2 | 4/2003 | Lieberman | | 6,866,664 B2 | 3/2005 | Schar et al. |
| 6,554,832 B2 | 4/2003 | Shluzas | | 6,866,682 B1 | 3/2005 | An et al. |
| 6,562,074 B2 | 5/2003 | Gerbec et al. | | 6,872,208 B1 | 3/2005 | McBride et al. |
| 6,565,574 B2 | 5/2003 | Michelson | | 6,875,211 B2 | 4/2005 | Nichols et al. |
| 6,575,981 B1 | 6/2003 | Boyd et al. | | 6,887,241 B1 | 5/2005 | McBride et al. |
| 6,582,432 B1 | 6/2003 | Michelson | | 6,890,334 B2 | 5/2005 | Brace et al. |
| 6,582,437 B2 | 6/2003 | Dorchak et al. | | 6,890,355 B2 | 5/2005 | Michelson |
| 6,585,749 B2 | 7/2003 | Hanson | | 6,899,734 B2 | 5/2005 | Castro et al. |
| 6,585,770 B1 | 7/2003 | White et al. | | 6,902,566 B2 | 6/2005 | Zucherman et al. |
| 6,595,995 B2 | 7/2003 | Zdeblick et al. | | 6,902,579 B2 | 6/2005 | Harms et al. |
| 6,602,253 B2 | 8/2003 | Richelsoph et al. | | 6,908,485 B2 | 6/2005 | Crozet et al. |
| 6,602,254 B2 | 8/2003 | Gertzbein | | 6,923,810 B1 | 8/2005 | Michelson |
| 6,607,557 B1 | 8/2003 | Brosnahan et al. | | 6,923,814 B1 | 8/2005 | Hildebrand et al. |
| 6,613,091 B1 | 9/2003 | Zdeblick et al. | | 6,923,830 B2 | 8/2005 | Michelson |
| 6,616,668 B2 | 9/2003 | Altarac et al. | | 6,929,662 B1 | 8/2005 | Messerli et al. |
| 6,616,671 B2 | 9/2003 | Landry et al. | | 6,958,066 B2 | 10/2005 | Richelsoph et al. |
| 6,641,583 B2 | 11/2003 | Shluzas et al. | | 6,960,212 B2 | 11/2005 | Richelsoph |
| 6,645,206 B1 | 11/2003 | Zdeblick et al. | | 6,981,975 B2 | 1/2006 | Michelson |
| 6,648,894 B2 | 11/2003 | Abdelgany et al. | | 6,991,653 B2 | 1/2006 | White et al. |
| 6,648,895 B2 | 11/2003 | Burkus et al. | | 6,991,654 B2 | 1/2006 | Foley |
| 6,648,915 B2 | 11/2003 | Sazy | | 6,997,953 B2 | 2/2006 | Chung et al. |
| 6,648,917 B2 | 11/2003 | Gerbec et al. | | 7,001,385 B2 | 2/2006 | Bonutti |
| 6,652,533 B2 | 11/2003 | O'Neil | | 7,014,659 B2 | 3/2006 | Boyer, II et al. |
| 6,652,584 B2 | 11/2003 | Michelson | | 7,022,138 B2 | 4/2006 | Mashburn |
| 6,660,038 B2 | 12/2003 | Boyer, II et al. | | 7,029,474 B2 | 4/2006 | Richelsoph et al. |
| 6,666,866 B2 | 12/2003 | Martz et al. | | 7,044,972 B2 | 5/2006 | Mathys, Jr. et al. |
| 6,673,073 B1 | 1/2004 | Schafer | | 7,056,343 B2 | 6/2006 | Schafer et al. |
| 6,676,703 B2 | 1/2004 | Biscup | | 7,063,725 B2 | 6/2006 | Foley |
| 6,679,887 B2 | 1/2004 | Nicholson et al. | | 7,066,938 B2 | 6/2006 | Slivka et al. |
| 6,682,534 B2 | 1/2004 | Patel et al. | | 7,077,864 B2 | 7/2006 | Byrd, III et al. |
| 6,692,495 B1 | 2/2004 | Zacouto | | 7,083,622 B2 | 8/2006 | Simonson |
| 6,699,248 B2 | 3/2004 | Jackson | | 7,087,083 B2 | 8/2006 | Pasquet et al. |
| 6,699,288 B2 | 3/2004 | Moret | | 7,104,993 B2 | 9/2006 | Baynham |
| 6,706,069 B2 | 3/2004 | Berger | | 7,118,571 B2 | 10/2006 | Kumar et al. |
| 6,709,458 B2 | 3/2004 | Michelson | | 7,128,762 B2 | 10/2006 | Middleton |
| 6,712,819 B2 | 3/2004 | Zucherman et al. | | 7,131,995 B2 | 11/2006 | Biedermann et al. |
| 6,712,852 B1 | 3/2004 | Chung et al. | | 7,135,025 B2 | 11/2006 | Pohjonen et al. |
| 6,716,247 B2 | 4/2004 | Michelson | | 7,135,042 B2 | 11/2006 | Stoll |
| 6,719,760 B2 | 4/2004 | Dorchak et al. | | 7,135,043 B2 | 11/2006 | Nakahara et al. |
| 6,719,794 B2 | 4/2004 | Gerber et al. | | 7,137,986 B2 | 11/2006 | Troxell et al. |
| 6,719,796 B2 | 4/2004 | Cohen et al. | | 7,137,997 B2 | 11/2006 | Paul |
| 6,723,096 B1 | 4/2004 | Dorchak et al. | | 7,141,068 B2 | 11/2006 | Ross et al. |
| 6,726,722 B2 | 4/2004 | Walkenhorst et al. | | 7,141,070 B2 | 11/2006 | Ralph et al. |
| 6,730,127 B2 | 5/2004 | Michelson | | 7,144,426 B2 | 12/2006 | Ralph et al. |
| 6,733,533 B1 | 5/2004 | Lozier | | 7,147,641 B2 | 12/2006 | Chen |
| 6,733,534 B2 | 5/2004 | Sherman | | 7,147,643 B2 | 12/2006 | Robioneck et al. |
| 6,733,535 B2 | 5/2004 | Michelson | | 7,153,304 B2 | 12/2006 | Robie et al. |
| 6,736,817 B2 | 5/2004 | Troxell | | 7,153,325 B2 | 12/2006 | Kim et al. |
| 6,740,089 B2 | 5/2004 | Haider | | 7,156,858 B2 | 1/2007 | Schuldt-Hempe et al. |
| 6,740,091 B2 | 5/2004 | Kohrs et al. | | 7,156,874 B2 | 1/2007 | Paponneau et al. |
| 6,743,232 B2 | 6/2004 | Overaker et al. | | 7,156,876 B2 | 1/2007 | Moumene et al. |
| 6,743,234 B2 | 6/2004 | Burkus et al. | | 7,160,301 B2 | 1/2007 | Cordaro |
| 6,746,454 B2 | 6/2004 | Winterbottom et al. | | 7,160,303 B2 | 1/2007 | Keller |
| 6,749,636 B2 | 6/2004 | Michelson | | 7,163,560 B2 | 1/2007 | Mason |
| 6,752,807 B2 | 6/2004 | Lin et al. | | 7,166,110 B2 | 1/2007 | Yundt |
| 6,752,832 B2 | 6/2004 | Neumann | | 7,166,129 B2 | 1/2007 | Michelson |
| 6,755,841 B2 | 6/2004 | Fraser et al. | | 7,166,130 B2 | 1/2007 | Ferree |
| 6,758,849 B1 | 7/2004 | Michelson | | 7,166,131 B2 | 1/2007 | Studer et al. |
| 6,758,862 B2 | 7/2004 | Berry et al. | | 7,169,181 B2 | 1/2007 | Kuras |
| 6,761,721 B2 | 7/2004 | Burgess et al. | | 7,169,182 B2 | 1/2007 | Errico et al. |
| 6,761,723 B2 | 7/2004 | Buttermann et al. | | 7,169,183 B2 | 1/2007 | Liu et al. |
| 6,764,491 B2 | 7/2004 | Frey et al. | | 7,172,595 B1 | 2/2007 | Goble |
| 6,764,514 B2 | 7/2004 | Li et al. | | 7,172,628 B2 | 2/2007 | Lamprich et al. |
| 6,776,798 B2 | 8/2004 | Camino et al. | | 7,179,295 B2 | 2/2007 | Kovacevic |
| 6,783,526 B1 | 8/2004 | Lin et al. | | 7,179,299 B2 | 2/2007 | Edwards et al. |
| 6,783,547 B2 | 8/2004 | Castro | | 7,182,781 B1 | 2/2007 | Bianchi et al. |
| RE38,614 E | 10/2004 | Paul et al. | | 7,182,783 B2 | 2/2007 | Trieu |
| 6,802,867 B2 | 10/2004 | Manasas et al. | | 7,182,784 B2 | 2/2007 | Evans et al. |
| 6,805,715 B2 | 10/2004 | Reuter et al. | | 7,189,242 B2 | 3/2007 | Boyd et al. |
| 6,808,538 B2 | 10/2004 | Paponneau | | 7,192,446 B2 | 3/2007 | Shapiro et al. |
| 6,824,565 B2 | 11/2004 | Muhanna et al. | | 7,192,447 B2 | 3/2007 | Rhoda |
| 6,840,941 B2 | 1/2005 | Rogers et al. | | 7,195,632 B2 | 3/2007 | Biedermann et al. |
| 6,843,804 B2 | 1/2005 | Bryan | | 7,195,643 B2 | 3/2007 | Jackson |
| 6,852,129 B2 | 2/2005 | Gerbec et al. | | 2001/0047208 A1 | 11/2001 | Michelson |
| 6,855,166 B2 | 2/2005 | Kohrs | | 2002/0007183 A1 | 1/2002 | Lee et al. |

| Publication No. | Date | Inventor |
|---|---|---|
| 2002/0026196 A1 | 2/2002 | Simon |
| 2002/0028192 A1 | 3/2002 | Dimitrijevich et al. |
| 2002/0055782 A1 | 5/2002 | Bagby |
| 2002/0111625 A1 | 8/2002 | Richelsoph et al. |
| 2002/0120274 A1 | 8/2002 | Overaker et al. |
| 2002/0143330 A1 | 10/2002 | Shluzas |
| 2002/0143400 A1 | 10/2002 | Biscup |
| 2002/0169448 A1 | 11/2002 | Vanacker |
| 2003/0018334 A1 | 1/2003 | Richelsoph et al. |
| 2003/0023244 A1 | 1/2003 | Richelsoph et al. |
| 2003/0023306 A1 | 1/2003 | Liu et al. |
| 2003/0028192 A1 | 2/2003 | Schar et al. |
| 2003/0045874 A1 | 3/2003 | Thomas, Jr. |
| 2003/0114853 A1 | 6/2003 | Burgess et al. |
| 2003/0125739 A1 | 7/2003 | Bagga et al. |
| 2003/0153917 A1 | 8/2003 | Richelsoph et al. |
| 2003/0167091 A1 | 9/2003 | Scharf |
| 2003/0167092 A1 | 9/2003 | Foley |
| 2003/0171813 A1 | 9/2003 | Kiester |
| 2003/0176925 A1 | 9/2003 | Paponneau |
| 2003/0176926 A1 | 9/2003 | Boehm, Jr. et al. |
| 2003/0181981 A1 | 9/2003 | Lemaire |
| 2003/0191531 A1 | 10/2003 | Berry et al. |
| 2003/0191535 A1 | 10/2003 | Castro |
| 2003/0195626 A1 | 10/2003 | Huppert |
| 2003/0195629 A1 | 10/2003 | Pafford et al. |
| 2003/0195632 A1 | 10/2003 | Foley et al. |
| 2003/0199983 A1 | 10/2003 | Michelson |
| 2004/0010315 A1 | 1/2004 | Song |
| 2004/0019356 A1 | 1/2004 | Fraser et al. |
| 2004/0030387 A1 | 2/2004 | Landry et al. |
| 2004/0034358 A1 | 2/2004 | Michelson |
| 2004/0034430 A1 | 2/2004 | Falahee |
| 2004/0049271 A1 | 3/2004 | Biedermann |
| 2004/0054412 A1 | 3/2004 | Gerbec et al. |
| 2004/0059419 A1 | 3/2004 | Michelson |
| 2004/0059420 A1 | 3/2004 | Michelson |
| 2004/0064185 A1 | 4/2004 | Michelson |
| 2004/0068259 A1 | 4/2004 | Michelson |
| 2004/0078078 A1 | 4/2004 | Shepard |
| 2004/0078079 A1 | 4/2004 | Foley |
| 2004/0082999 A1 | 4/2004 | Mathys, Jr. et al. |
| 2004/0088054 A1 | 5/2004 | Berry |
| 2004/0093083 A1 | 5/2004 | Branch et al. |
| 2004/0093084 A1 | 5/2004 | Michelson |
| 2004/0093085 A1 | 5/2004 | Michelson |
| 2004/0093086 A1 | 5/2004 | Michelson |
| 2004/0097928 A1 | 5/2004 | Zdeblick et al. |
| 2004/0097929 A1 | 5/2004 | Branch et al. |
| 2004/0102848 A1 | 5/2004 | Michelson |
| 2004/0116928 A1 | 6/2004 | Young et al. |
| 2004/0117017 A1 | 6/2004 | Pasquet et al. |
| 2004/0117018 A1 | 6/2004 | Michelson |
| 2004/0133203 A1 | 7/2004 | Young et al. |
| 2004/0133280 A1 | 7/2004 | Trieu |
| 2004/0236427 A1 | 11/2004 | Berry et al. |
| 2005/0010294 A1 | 1/2005 | Michelson |
| 2005/0015097 A1 | 1/2005 | Mujwid et al. |
| 2005/0049706 A1 | 3/2005 | Brodke et al. |
| 2005/0070899 A1 | 3/2005 | Doubler et al. |
| 2005/0080416 A1 | 4/2005 | Ryan et al. |
| 2005/0096745 A1 | 5/2005 | Andre et al. |
| 2005/0131419 A1 | 6/2005 | McCord et al. |
| 2005/0137594 A1 | 6/2005 | Doubler et al. |
| 2005/0159813 A1 | 7/2005 | Molz, IV |
| 2005/0216088 A1 | 9/2005 | McKinley et al. |
| 2005/0228326 A1 | 10/2005 | Kalfas et al. |
| 2005/0228377 A1 | 10/2005 | Chao et al. |
| 2005/0283236 A1 | 12/2005 | Razian |
| 2006/0058879 A1 | 3/2006 | Metz-Stavenhagen |
| 2006/0064091 A1 | 3/2006 | Ludwig et al. |
| 2006/0116770 A1 | 6/2006 | White et al. |
| 2006/0241602 A1 | 10/2006 | Jackson |
| 2007/0016197 A1 | 1/2007 | Woods |

FOREIGN PATENT DOCUMENTS

| | | |
|---|---|---|
| CA | 2015507 | 1/1999 |
| DE | 2750648 | 5/1979 |
| DE | 3023942 | 1/1982 |
| DE | 3741487 | 6/1989 |
| DE | 4012622 | 7/1991 |
| DE | 4323595 | 7/1994 |
| DE | 19500170 | 2/1996 |
| DE | 19604246 | 8/1996 |
| DE | 19622827 | 12/1997 |
| EP | 0179695 | 4/1986 |
| EP | 0290767 | 11/1988 |
| EP | 0369603 | 10/1989 |
| EP | 0490159 | 11/1991 |
| EP | 0517030 | 5/1992 |
| EP | 0706876 | 9/1995 |
| EP | 0716840 | 12/1995 |
| EP | 1400221 | 6/1996 |
| EP | 0796593 | 3/1997 |
| EP | 0880938 | 5/1998 |
| EP | 1100417 | 2/2000 |
| EP | 1080703 | 8/2000 |
| EP | 1430857 | 12/2002 |
| EP | 1430858 | 12/2002 |
| EP | 1346709 | 3/2003 |
| EP | 0878170 B1 | 7/2003 |
| EP | 0878171 B1 | 7/2003 |
| EP | 1398008 | 7/2003 |
| EP | 1334703 A2 | 8/2003 |
| EP | 1391188 | 8/2003 |
| EP | 1391189 | 8/2003 |
| EP | 1415622 | 9/2003 |
| EP | 1415623 | 9/2003 |
| EP | 1410770 | 4/2004 |
| EP | 1297792 B1 | 1/2005 |
| JP | 2002305068 | 10/2002 |
| JP | 2003305068 | 10/2003 |
| WO | 9106261 | 5/1991 |
| WO | 9201428 | 2/1992 |
| WO | 9404100 | 3/1994 |
| WO | 9418913 | 9/1994 |
| WO | 9501810 | 1/1995 |
| WO | 9608205 | 3/1996 |
| WO | 9640020 | 12/1996 |
| WO | 9641582 | 12/1996 |
| WO | 9733525 | 9/1997 |
| WO | 9809586 | 3/1998 |
| WO | 9814142 | 4/1998 |
| WO | 9817208 | 4/1998 |
| WO | 9834552 | 8/1998 |
| WO | 9932054 | 1/1999 |
| WO | 9907312 | 2/1999 |
| WO | 9908627 | 2/1999 |
| WO | 9932055 | 7/1999 |
| WO | 9938461 | 8/1999 |
| WO | 9956675 | 11/1999 |
| WO | 0007527 | 2/2000 |
| WO | 0023013 | 4/2000 |
| WO | 0106962 | 2/2001 |
| WO | 0209786 | 2/2002 |
| WO | 0219952 | 3/2002 |
| WO | 0238086 | 5/2002 |
| WO | 02060356 | 8/2002 |
| WO | 02076335 | 10/2002 |
| WO | 02078514 | 10/2002 |
| WO | 03009786 | 2/2003 |
| WO | 03013399 | 2/2003 |
| WO | 03020143 | 3/2003 |
| WO | 03026522 | 4/2003 |
| WO | 03026538 | 4/2003 |
| WO | 03068112 | 8/2003 |
| WO | 03071998 A3 | 9/2003 |
| WO | 03096937 | 11/2003 |
| WO | 2004000177 | 12/2003 |
| WO | 2004008999 | 1/2004 |
| WO | 2004024038 | 3/2004 |
| WO | 2004026188 | 4/2004 |
| WO | 2004041130 | 5/2004 |
| WO | 2004043306 | 5/2004 |
| WO | 2004052245 | 6/2004 |

* cited by examiner

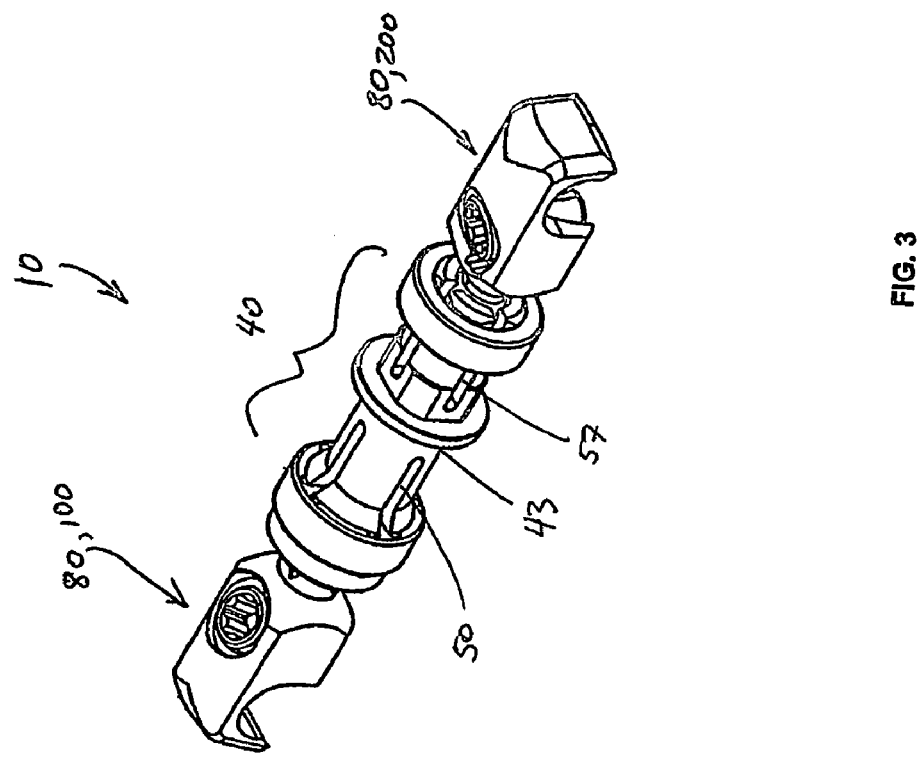
FIG. 3
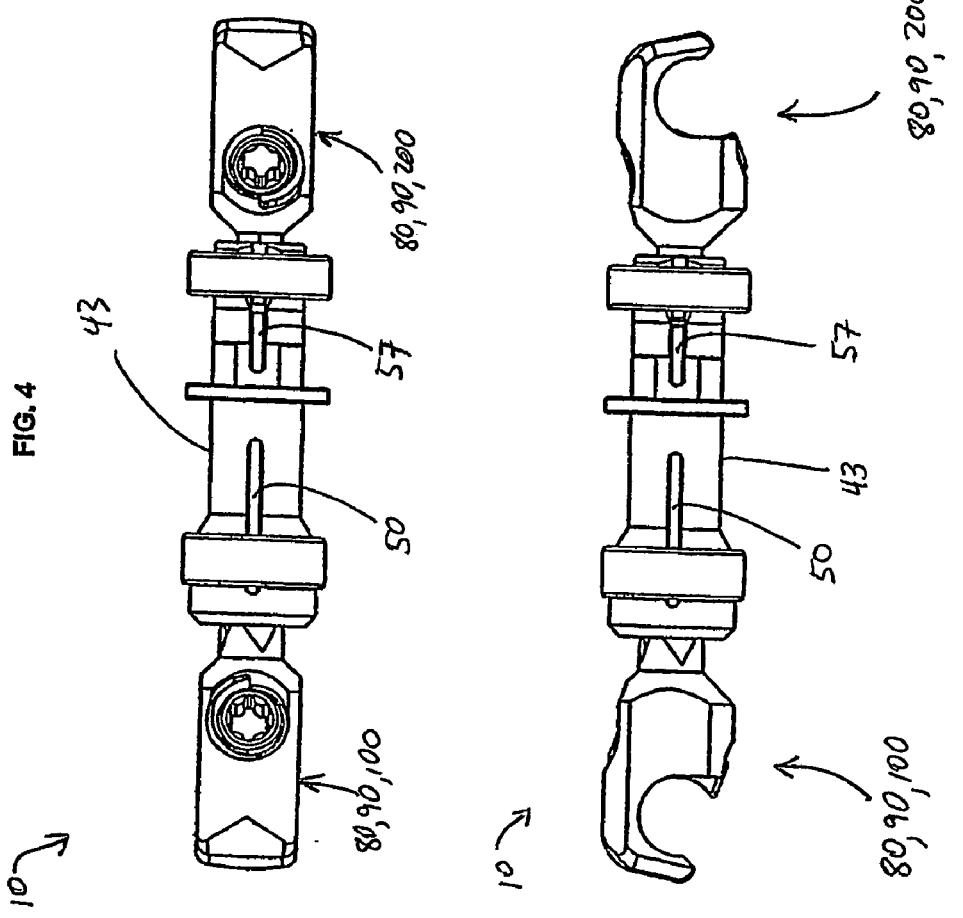
FIG. 4
FIG. 5

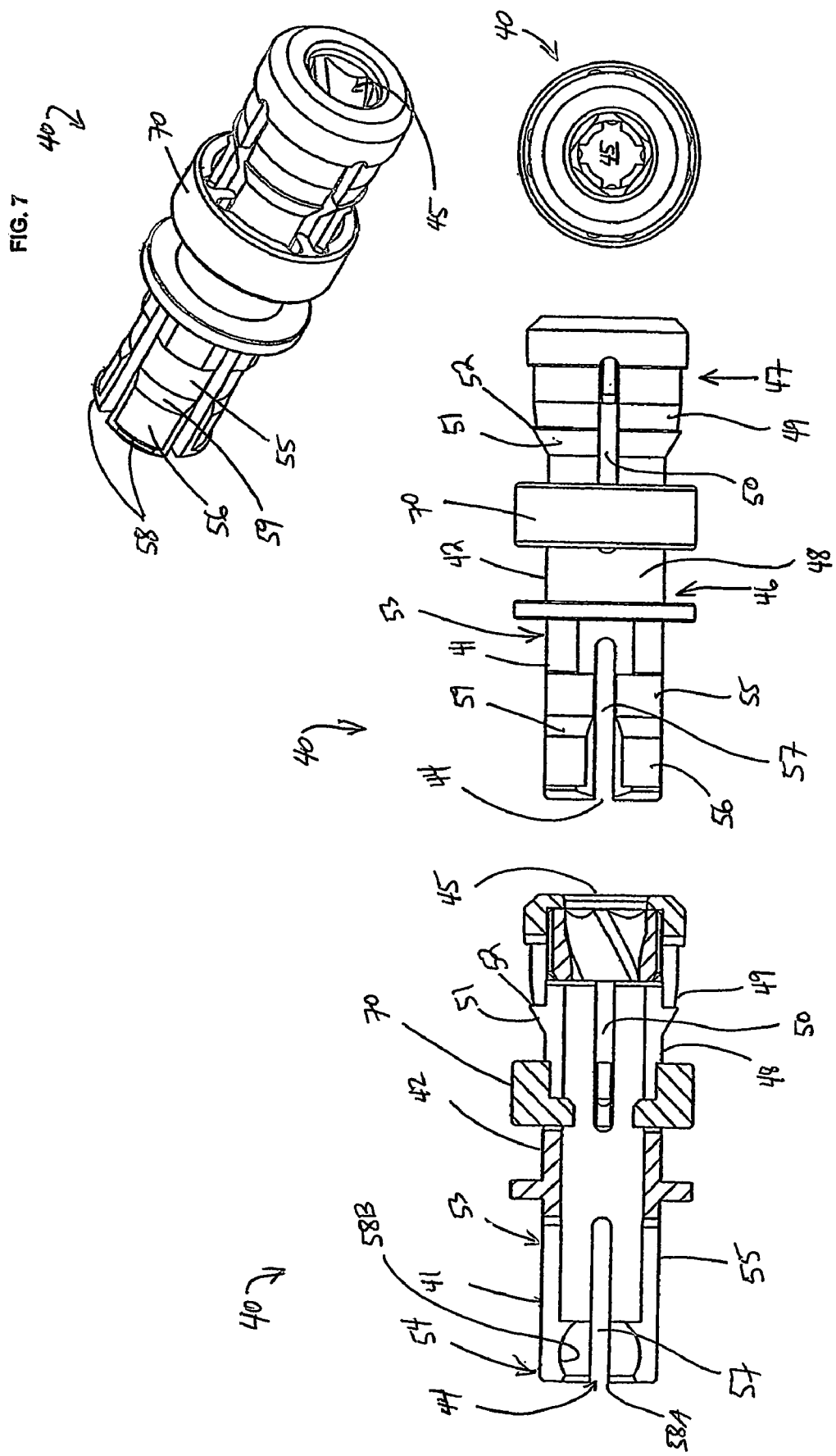

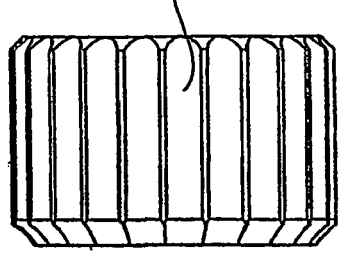
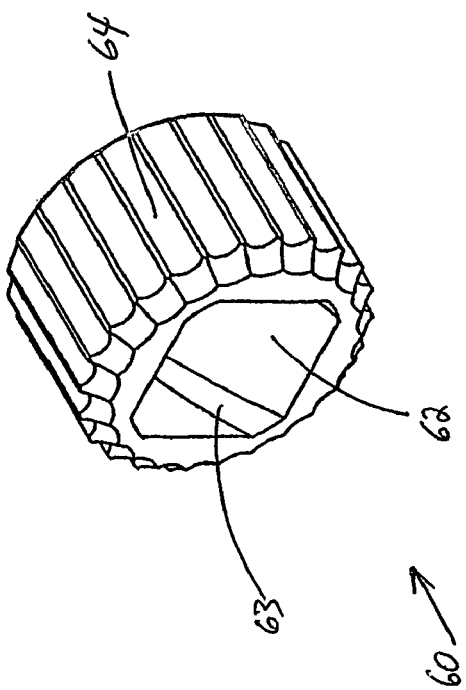
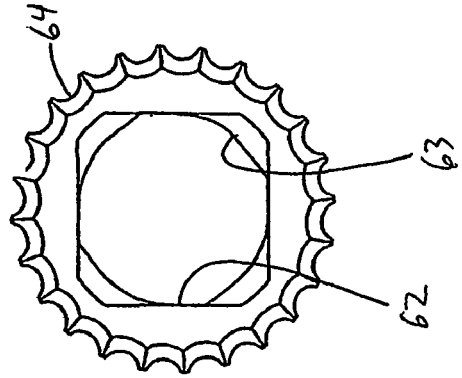
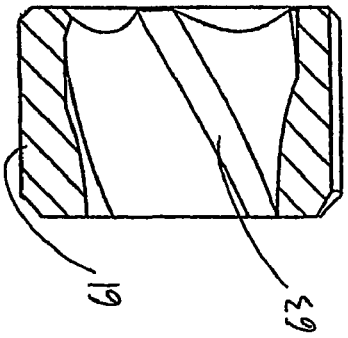

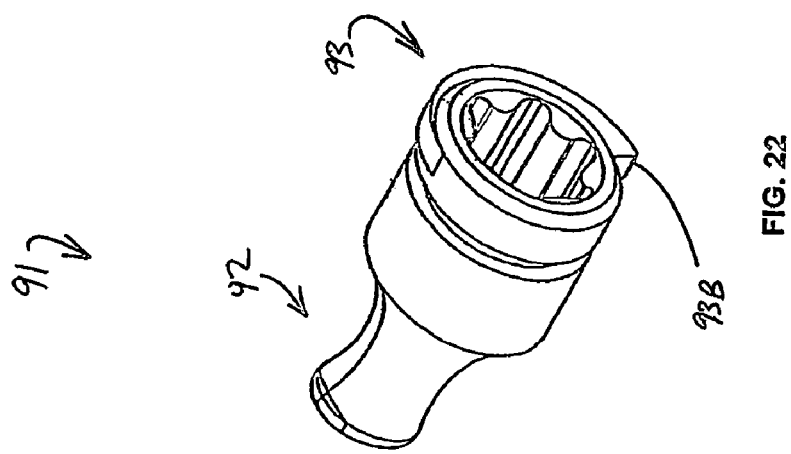
FIG. 22
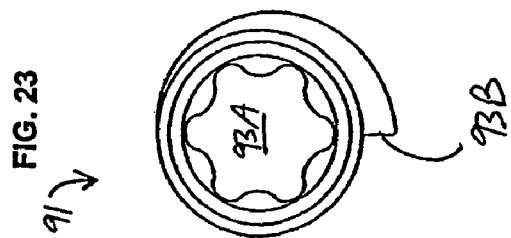
FIG. 23
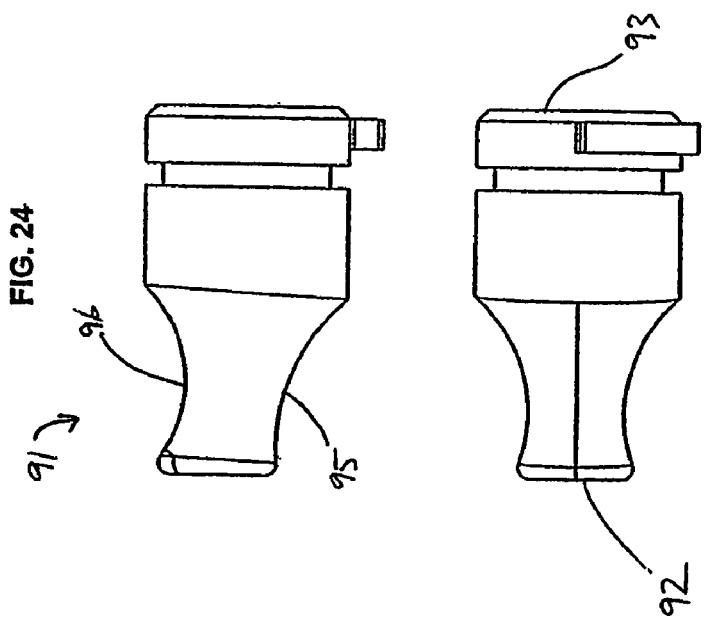
FIG. 24
FIG. 25
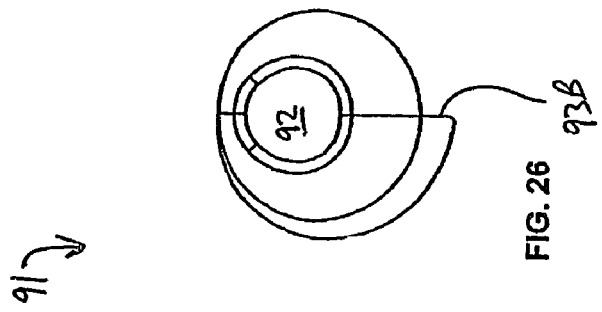
FIG. 26

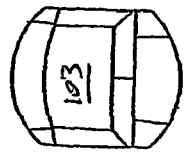
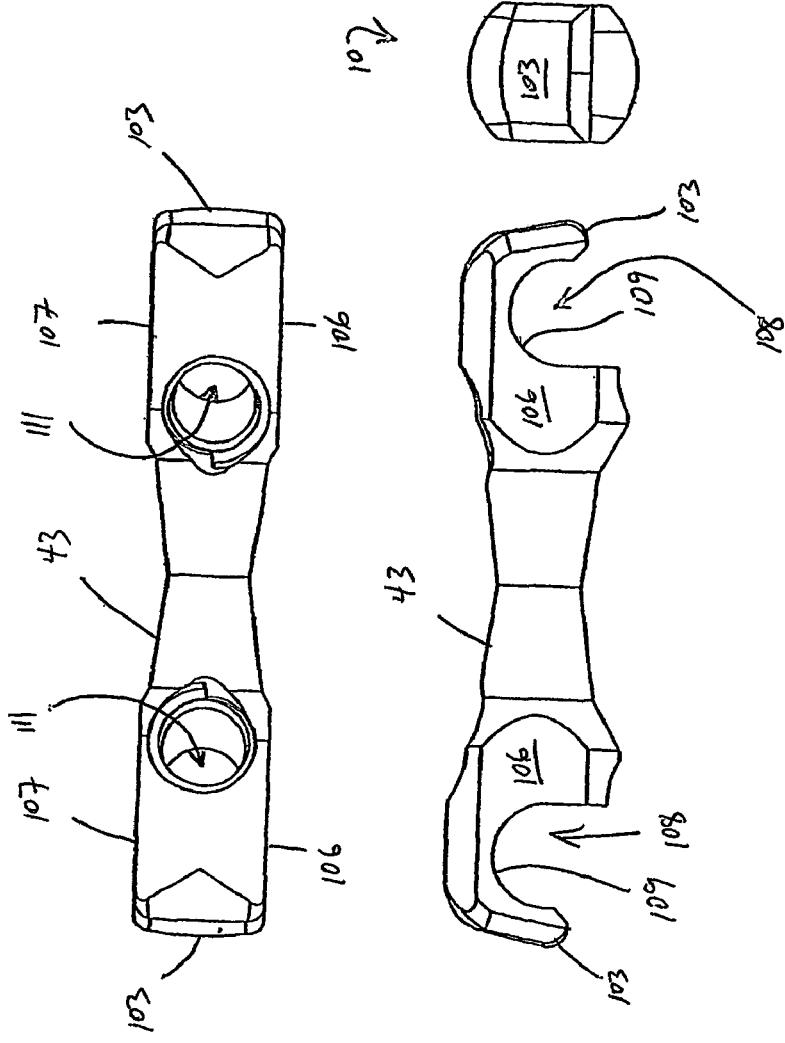
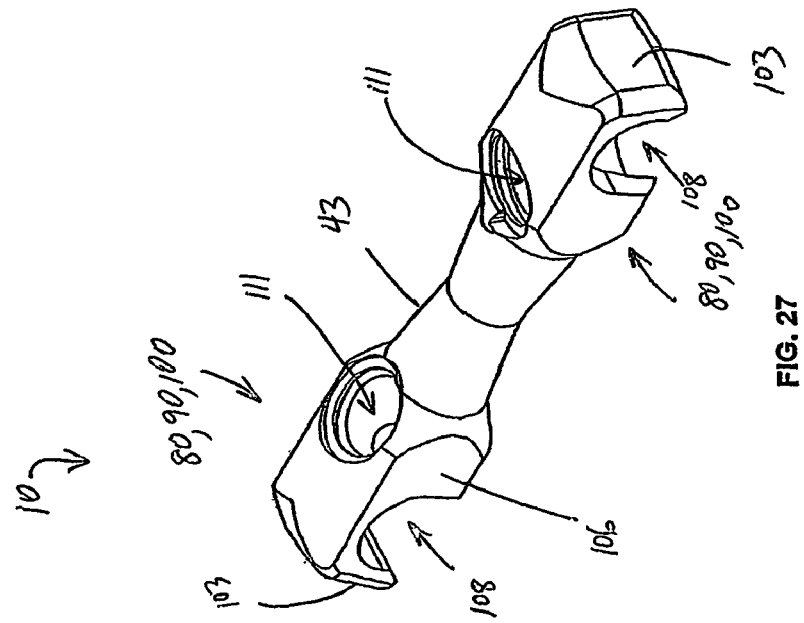

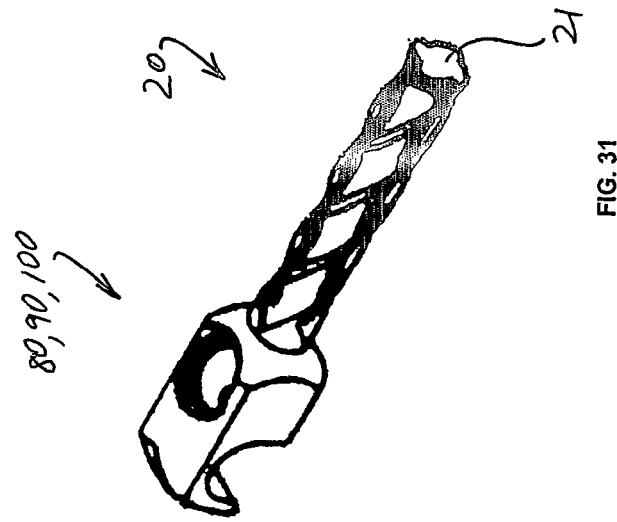
FIG. 31
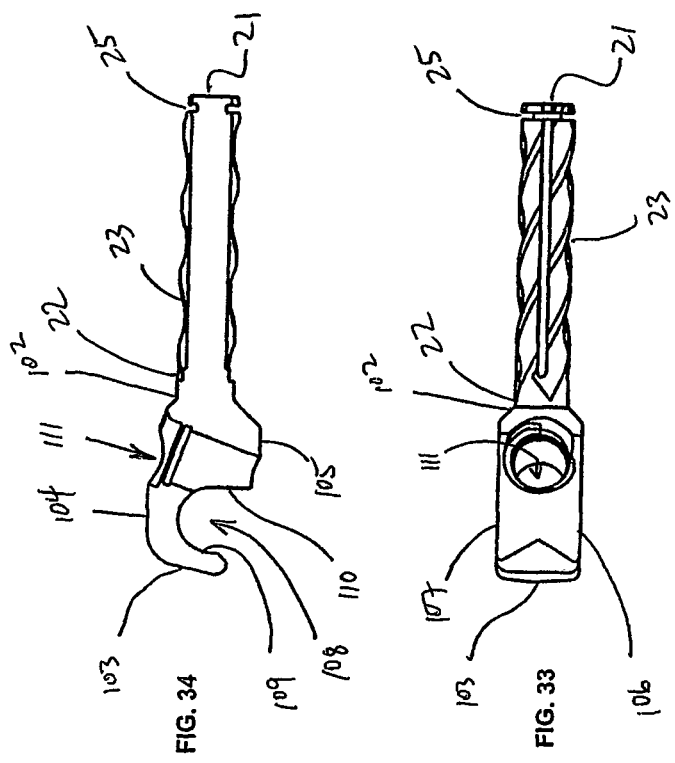
FIG. 34
FIG. 33
FIG. 32

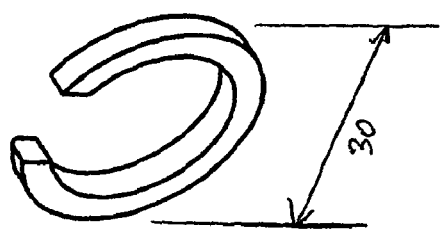
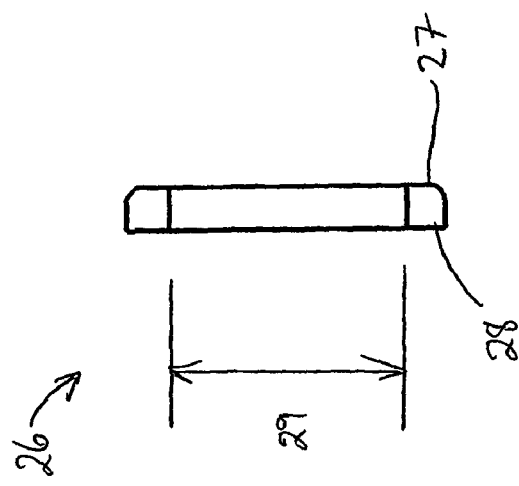

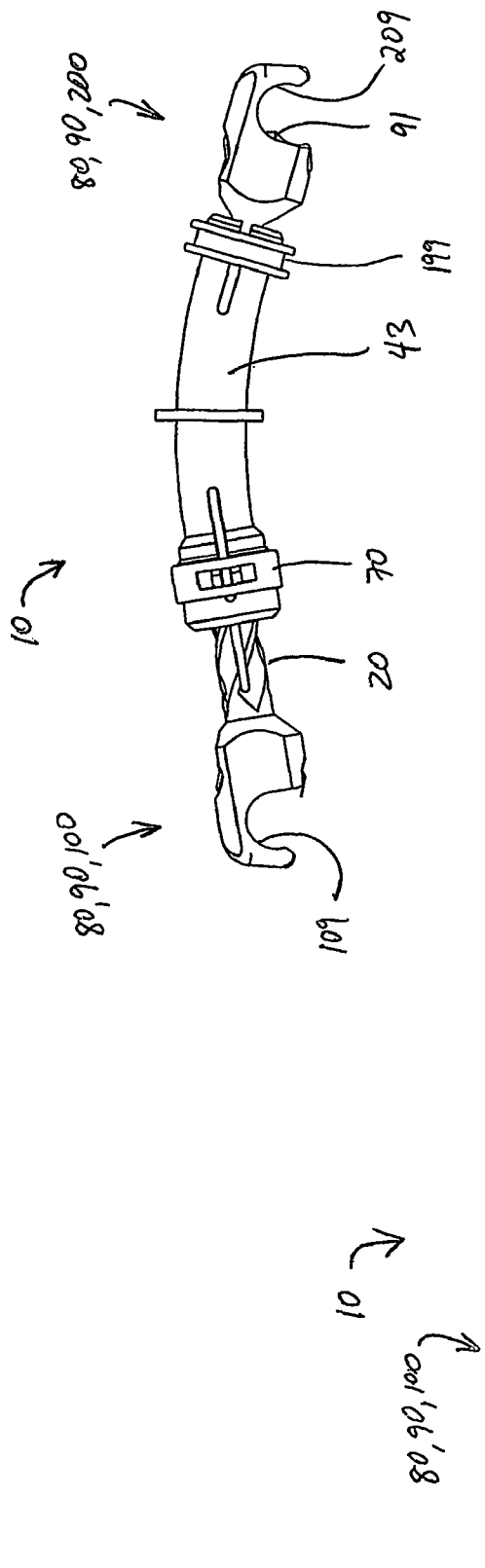
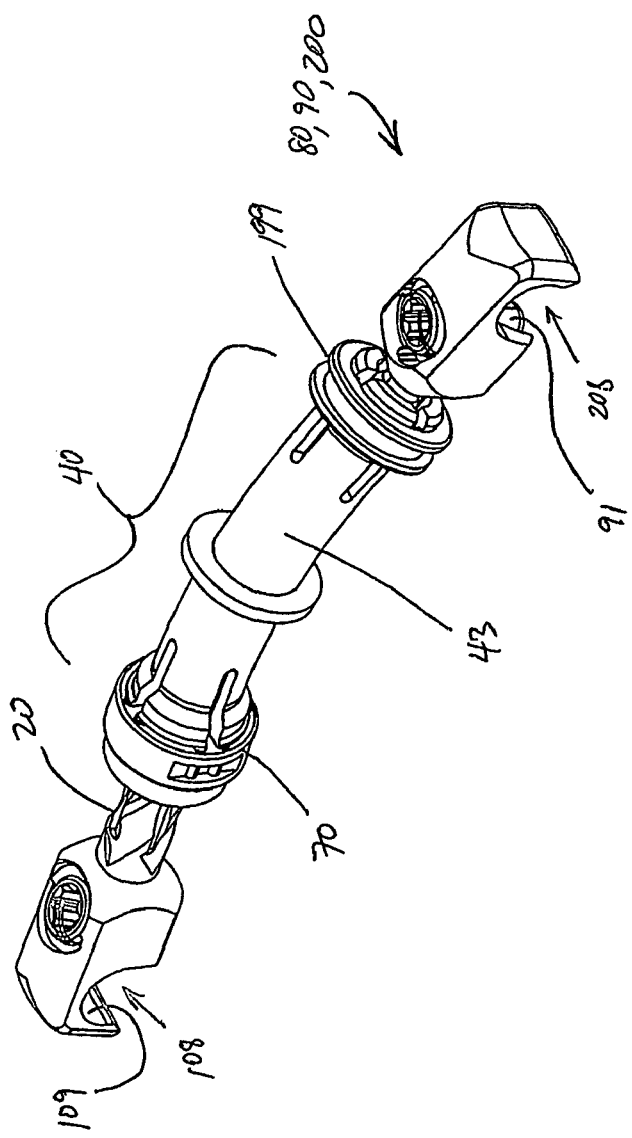
FIG. 46
FIG. 45

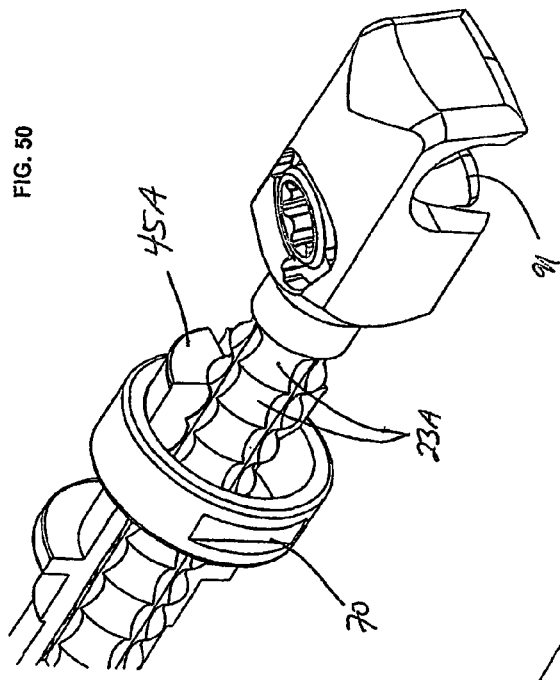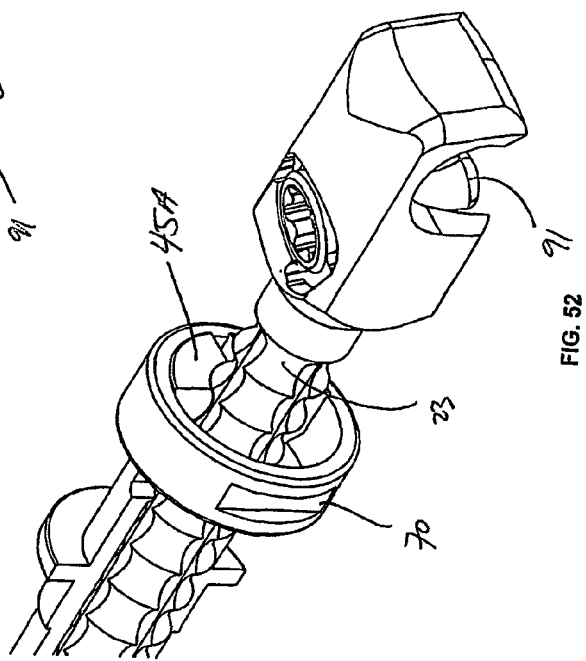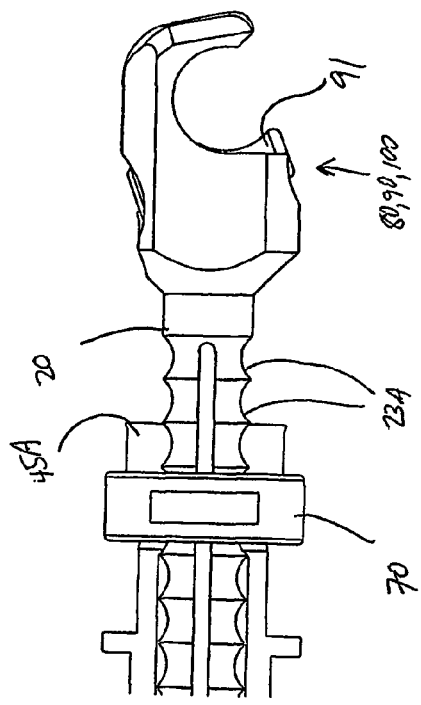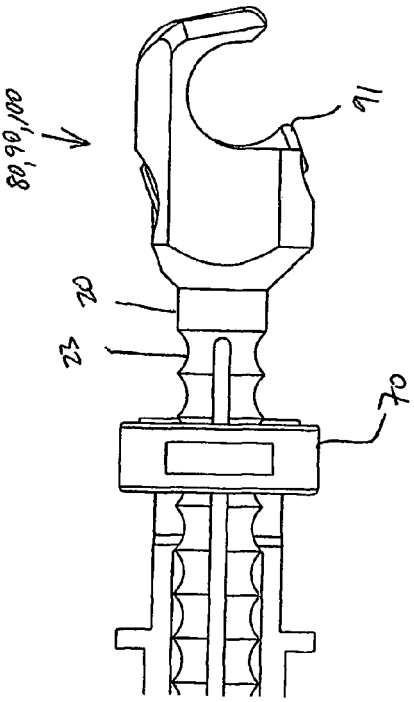

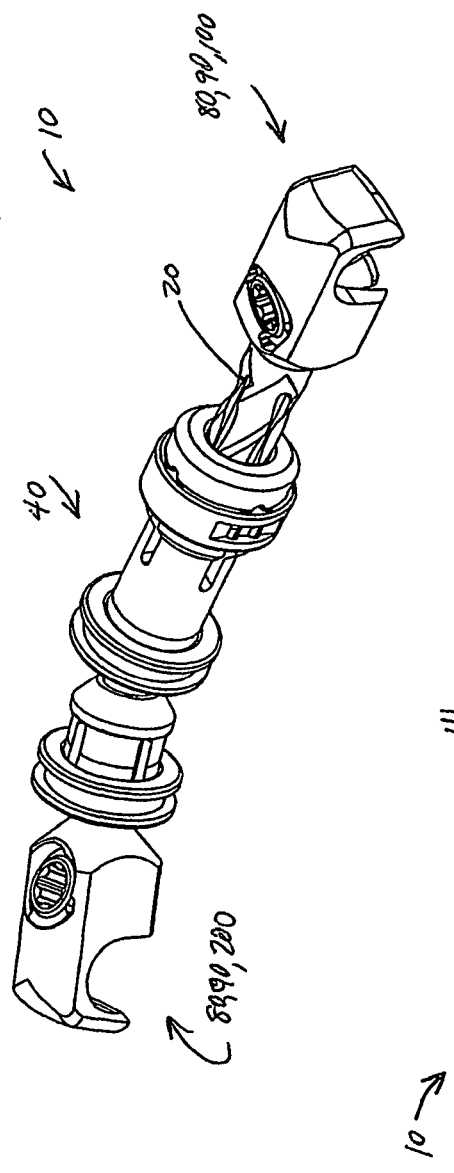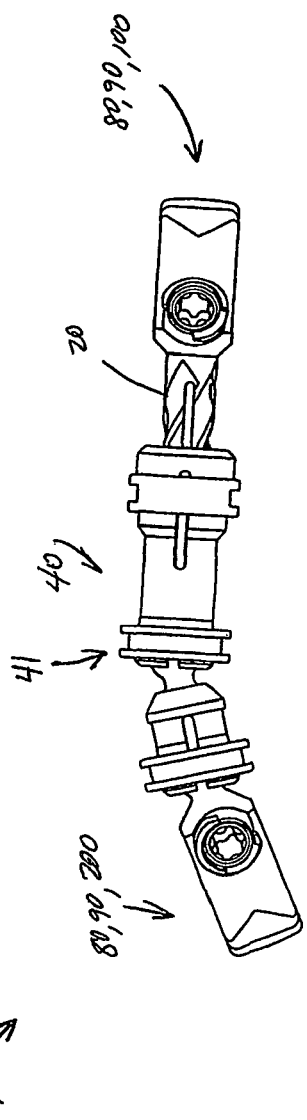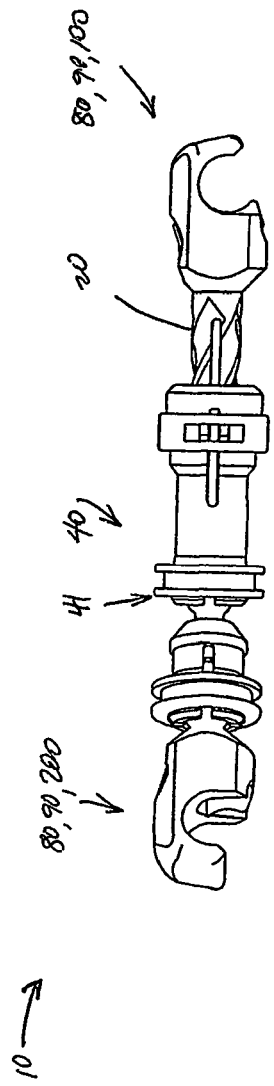
FIG. 58
FIG. 60
FIG. 59

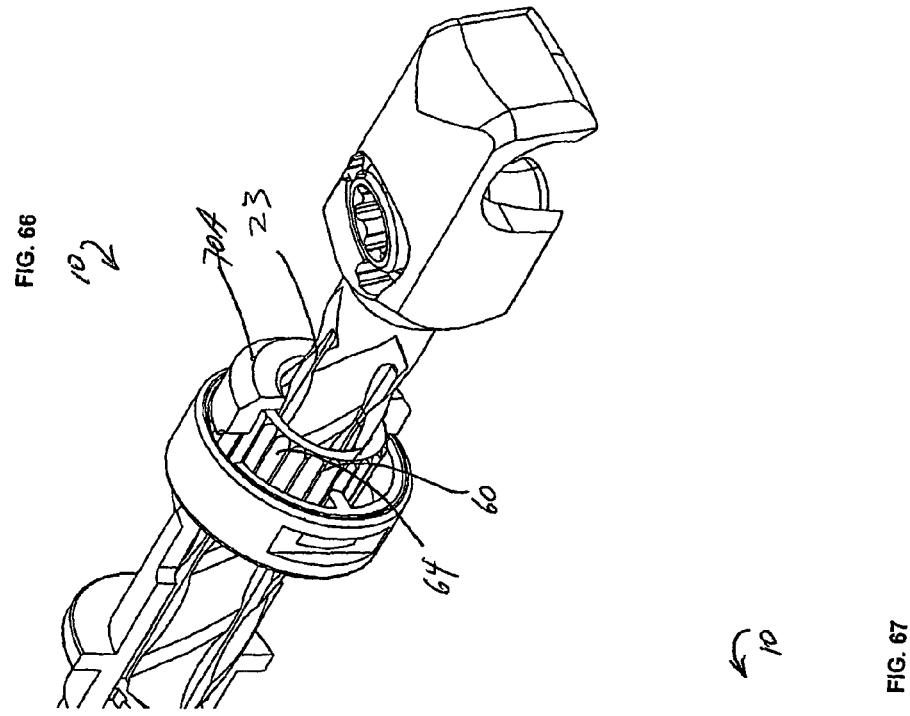
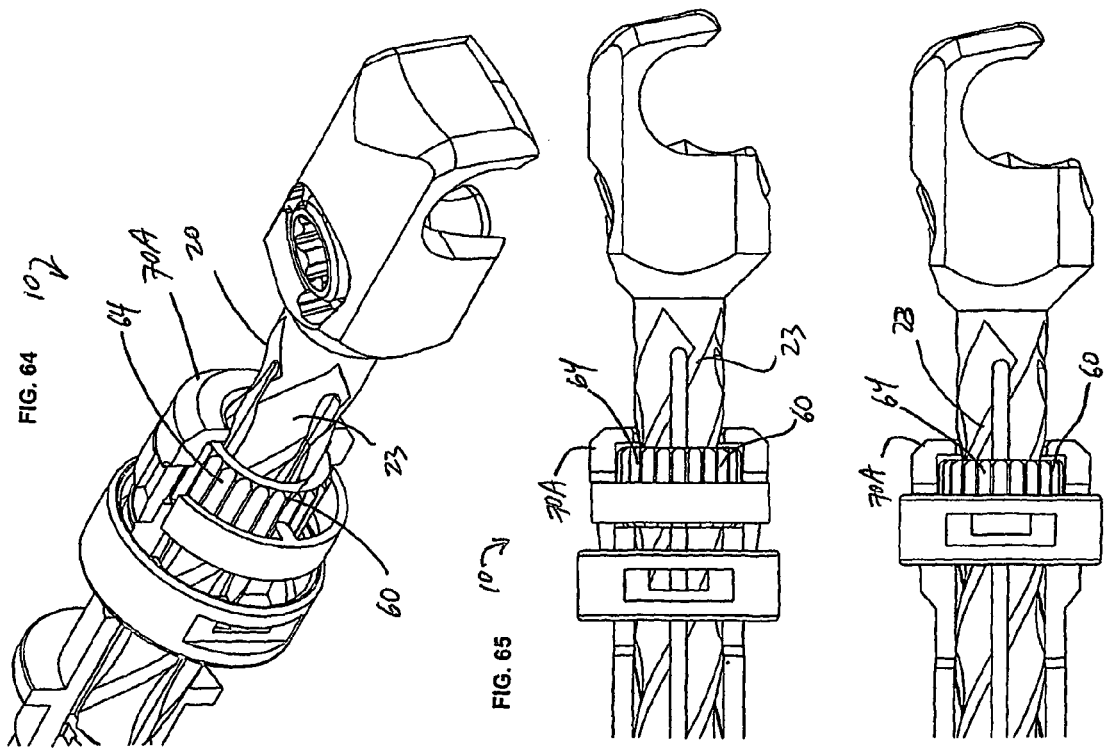

SPINAL IMPLANT ADJUSTMENT DEVICE

BACKGROUND OF THE INVENTION

1. Field of the Invention

The present invention generally relates to a device for spinal fixation, and in particular to an adjustment device for many types of spinal implants. The device finds particularly suitable applications in spinal fusion devices such as a connector for coupling elongate members (such as spinal rods), plates, and the like, as well as in adjustable vertebral spacers for intervertebral fusion devices, corpectomy devices, and other vertebral prostheses.

2. Background

The spinal column is a complex system of bones in stacked relation held upright by fibrous bands called ligaments and contractile elements called muscles. This column is critical for protecting the delicate spinal cord and nerves and for providing structural support for the entire body. There are seven bones in the neck (cervical) region, twelve bones in the chest (thoracic) region, and five bones in the low back (lumbar) region. There are also five bones in the pelvic (sacral) region which are normally fused together and form the back part of the pelvis. Each vertebra has a roughly cylindrical body with wing-like projections and a bony arch. The arches, which are positioned next to one another, create a tunnel-like space which houses the spinal cord. The anterior cylindrical bodies of the vertebrae, which are spaced apart by intervertebral discs, bear most of the compressive load of the spinal column. The spinal column is also flexible and is capable of a high degree of curvature and twist through a wide range of motion.

It is often necessary to surgically treat spinal disorders, such as scoliosis, as well as to surgically correct spinal problems such as those that occur due to trauma, developmental irregularities, or disease. Numerous systems are known for use in spinal correction and fixation, depending on the type of problem sought to be solved.

Spinal fusion (arthrodesis) devices attempt to restore stability to the spine by fusion in the problem area. These systems generally employ spinal instrumentation having connective structures such as one or more plates or rods that are placed on portions of the spinal column near the area intended to be fused. These systems usually include attachment devices including, but not limited to, pedicle screws, transverse process hooks, sublaminar hooks, pedicle hooks, and other similar devices. Rod systems, of which there are several, are frequently used in spine stabilization. Typically, the rods are utilized in pairs longitudinally along the length of the spinal column. For the sake of simplicity, the term "rod" will be used throughout to refer to any elongate or longitudinal member.

It is known that the strength and stability of a dual rod assembly can be increased by coupling the two rods with a cross-brace or connector that extends substantially perpendicular to the longitudinal axes of the rods across the spine. The simplest situation in which a connector could be used occurs when the two rods are geometrically aligned. Specifically, the two rods are parallel to each other, that is, there is no rod convergence or divergence in the medial-lateral direction. Stated alternatively, the two rods have the same orientation with respect to the coronal plane (viewed in the anterior-posterior direction); or, the rods are coplanar from a lateral view; and the two rods are located a uniform distance from each other.

In reality, spinal rods are rarely geometrically aligned in the above-mentioned simplest situation. The actual variations of geometrical alignment must be accommodated in some fashion. One way to accommodate actual arrangement is for one or both of the rods to be bent to accommodate the connector. However, any bending in either of the rods can adversely affect the fixation to the spine and compromise clinical outcome. Furthermore, the bending can adversely affect the mechanical properties of the rods, not to mention the fact that bending is both difficult and time-consuming for the surgeon. The connector can also be bent so that the disturbance to the rod positioning is minimized. Unfortunately, this too can cause the mechanical properties of the connector to be compromised.

To remedy these concerns, connectors with some adjustability have been designed to adapt for variations from the simplest geometrical alignment. One major problem with current devices is that those that do provide some form of length adjustability utilize inferior locking designs. Some utilize a slideable member with a pin anchor. Others use a slideable member with a compression style lock. The former style is cumbersome and runs the risk of pin-removal. The latter style is cumbersome and provides inadequate locking strength. In fact, most require the surgeon to impart a large amount of force on the construct in order to engage the lock. Despite engagement of these locking devices, none of these types of locking devices has been shown to adequately positively lock the length.

Another major problem with the current devices is that the method of locking the rod to the connector is inefficient or inadequate. Many current devices utilize threaded set screws that engage an exterior surface of the rod. Threading the set screw into the set screw opening applies a compressive force on the rod, which is supposed to secure the rod. Several problems exist with these threaded connections, including cross-threading, loosening over time, and the structural deformities imposed on the surface of the rod that is contacted by the set screw. Another current device uses a clamp body having opposable arms and utilizes a cam lug to force the arms closed in a scissors-like action to compressively load the rod. Yet another device utilizes a yoke-like clamping body disposed in a through-bore having resilient sidewalls that provide a wedging effect on the rod upon tightening of a locking screw in the through-bore. None of these devices, however, provide the simple, secure locking fit desired to positively retain a rod in situ long term.

An additional problem with these types of devices is that they are typically multi-piece systems that can be difficult to assemble and use in the surgical environment. And, even those that are one-piece designs do not allow for adjustments to compensate for all three modes in which there may be variation from geometrical alignment: convergence or divergence in the medial-lateral plane, non-coplanar rods, and variability in rod separation distances. For example, U.S. Pat. No. 5,947,966 discloses a device for linking adjacent spinal rods. In one embodiment, the device includes two members that are movable with respect to one another to accommodate different rod separation distances. A pin on one member engages a groove on the other member to provisionally couple the two members, thereby preventing a surgeon from separating the two members. Because the pin is sized to exactly fit the groove, no movement of the pin transverse to the longitudinal axis of the groove is possible. As a result, the device disclosed in the '966 patent cannot accommodate non-coplanar rods or adjust for rod convergence or divergence.

In some spinal surgeries, different types of devices are used to maintain the normal spacing between vertebrae, as well as to alleviate compression of the spinal cord. These devices are known as corpectomy devices and are typically inserted into a cavity created when all or a portion of one or more vertebrae are removed. One example of corpectomy devices are hollow mesh cages filled with bone chips or marrow, or even artificial bone material. Limitations of most present-day intervertebral implants are significant and revolve largely around the marked variation in disc space shape and height that results from either biologic variability or pathologic change. For example, if a disc space is 20 mm in height, a cylindrical implant bridging this gap requires a minimum height of 20 mm just to contact the end plate of the vertebral bone. Generally, end plate disruption must occur to allow a generous bony union, meaning that an additional 2-3 mm must be added on each end, resulting in a final implant size of 24-26 mm. During implantation from an anterior approach, excessive retraction is often required on the great blood vessels which significantly enhances the risk of devastating complications such as vascular tears or thrombosis. On the other hand, during a posterior approach, large implants may require excessive traction on neural elements for adequate placement, even if all posterior bony elements are removed. In some instances, an adequate implant size cannot be inserted posteriorly, particularly if there is a significant degree of ligamentous laxity requiring higher degrees of distraction to obtain stability by tightening the annular ligamentous tension band. Compromising on implant size risks sub-optimal stability or a loose implant, which has a greater chance for migration within or expulsion from the disc space. The alternative of excessively retracting neural elements to facilitate a posterior implant application results in a neuropraxia at best and permanent neural damage at worst.

Thus the need exists for an adjustable corpectomy that is simple to use in clinical procedures and that adequately and effectively spans the distance between vertebral bodies, is easily adjustable to account for space variability, and provides a secure lock once the desired dimension is achieved. Additionally, the need exists for an improved connector for spinal rods that can allow adjustability in all geometrical arrangements; that can provide quick and secure locking of the rod; and that provides a simple, positive locking length-adjusting mechanism that does not rely on compression fit or pin locking mechanisms.

BRIEF SUMMARY OF THE INVENTION

The present invention generally relates to devices for spinal fixation, and in particular to adjustable devices for use as connectors for coupling spinal rods or other elongate members; as well as for use as corpectomy devices and the like. Various embodiments are discussed, with the primary invention being utilized in different types of implants. As used herein, the general term "connector" shall refer to the device in its many embodiments, regardless whether the device is being used to connect elongate members (as in spinal rod systems) or to span the distance between two vertebral bodies (as in corpectomy devices). The connector generally comprises a two-piece body having an extending shaft and a housing; a rotor; and a locking collar. The terminal ends of each connector may be fitted with a fixed rod-receiving jaw, an articulating rod-receiving jaw, or simply with endplates or other structures of various designs having bone receiving surfaces thereon.

In a first embodiment the extending shaft has an external surface containing thereon a helical profile. The rotor likewise has an internal surface containing thereon one or more helical surfaces that correspond to the external surface of the extending shaft. The internal helical surface of the rotor is placed in intimate contact with the external helical surface of an extending shaft. This intimate contact couples the rotor to the extending shaft such that translational movement of the extending shaft results in rotation of the rotor, and vice versa. Similarly, preventing movement of either the extending shaft or the rotor automatically prevents movement of the other.

The rotor is a substantially cylindrical body that has axial grooves disposed about its circumference. The locking collar is also a substantially cylindrical member having at least one protrusion disposed radially on the internal surface thereof. When the extending shaft is translated into or out of the body, the helical surface causes the rotor to spin inside the housing. When the desired length of the connector is achieved, the locking collar is moved from its unlocked position to its locked position, wherein the at least one protrusion engages the grooves on the rotor's circumference. Once a protrusion is inside a groove, rotational movement of the rotor is prevented, which thereby prevents axial movement of the extending shaft. This provides a positive lock for the extending shaft (and therefore for the length of the connector) without the need for a compression fit and without requiring the surgeon to impart large forces onto the construct.

In another aspect of the invention, a unique locking cam is provided at each jaw to secure a rod to the connector. The locking cam generally comprises a substantially cylindrical body having an engaging end and a driving end. The engaging end has a combination concave surface having differing curvatures disposed about its circumference, or simply having curvatures disposed at different points on the surface. The driving end has a cavity to receive a driving instrument and an appurtenant stop disposed at a location along its perimeter. The jaw comprises an opening to receive the locking cam therein. The opening is preferably substantially cylindrical having a discontinuity disposed out of phase with the appurtenant stop. Upon insertion of the cam into the opening, the driving instrument turns the cam the desired amount (preferably 180 degrees). This turning rotates the engaging end about the cam's axis of rotation, which brings the cam into tighter engagement with the rod as the combination curvatures rotate into engagement with the outer surface of the rod. Once the cam is fully turned, the stop engages the discontinuity, which visually and tacitly informs the surgeon that the cam is locked.

In another aspect of the invention, an articulating jaw is provided. The articulating jaw itself comprises a jaw with a locking cam on one end and a ball-shaped protrusion on the other end. The terminal end of the connector comprises a substantially cylindrical member having an axial opening therein and comprising axial fingers for receiving the ball of an articulating jaw. The axial fingers are deflectable inwardly by a locking collar. The locking collar is disposed about the external surface of the fingers and is slideable between a first unlocked position and a second locked position. In the second position, the articulating jaw locking collar imparts a radial compressive force on the surface of the ball, thereby locking it into position. This can be achieved in various ways, including shaping the external surface of the fingers with an increasing diameter toward the distal ends thereof, such that as the articulating jaw locking collar moves distally, it rides along the increasing diameter, thus forcing the internal surface into compressive contact with the ball. Additionally the articulating locking collar itself may be fitted with an inner surface that has an increasing diameter in the locked direction. Many other structural combinations are possible to achieve this effect, the end result being to lock the ball in a given orientation. The articulating jaw can therefore assume any number of angles to better facilitate the rod.

The articulating jaw therefore forms a ball and socket joint that enables movement to allow the connector to join rods that are not parallel. Alternatively, the ball-shaped protrusion may be fitted on the body of the connector and the jaw may have the corresponding socket to provide the ball and socket union.

In another aspect of the invention, a fixed length connector is provided. The connector comprises a solid shaft with jaws on either end. The shaft is made from titanium or any material suitable for implantation. The jaws maybe of the fixed or articulating variety as described.

In another embodiment of the invention the jaws comprise endplates or other structures to be used to engage vertebral bodies or other bony structures. The endplates can be fixed or variable to allow for better anatomical fit.

Alternative embodiments are also depicted utilizing pre-bent connectors; connectors utilizing multiple articulating jaws; connectors using grooved extending shafts; connectors using helical ratcheting shafts; connectors using a taper lock; and connectors utilizing a pivoting body.

BRIEF DESCRIPTION OF THE DRAWINGS

The teachings of the present invention can be readily understood by considering the following detailed description in conjunction with the accompanying drawings, in which:

FIG. 3 is a perspective view of a connector according to an embodiment of the invention having one fixed jaw and one articulating jaw;

FIG. 4 is a top plan view of the connector shown in FIG. 3;

FIG. 5 is a side elevation view of the connector shown in FIG. 3;

FIG. 7 is a perspective view of the two-piece body of a connector according to an embodiment of the invention;

FIG. 8 is a section view of the connector shown in FIG. 7;

FIG. 9 is a side elevation view of the connector shown in FIG. 7;

FIG. 10 is an end view of the connector shown in FIG. 7 looking into the second axial opening;

FIG. 11 is a perspective view of a rotor according to an embodiment of the invention;

FIG. 12 is a side elevation view of the rotor shown in FIG. 11;

FIG. 13 is an end view of the rotor shown in FIG. 11;

FIG. 14 is a side elevation view in section of the rotor shown in FIG. 11;

FIG. 22 is a perspective view of a locking cam according to an embodiment of the invention;

FIG. 23 is a driving end axial view of the locking cam of FIG. 22;

FIG. 24 is a side elevation view of the locking cam of FIG. 22;

FIG. 25 is a bottom elevation view of the locking cam of FIG. 22;

FIG. 26 is an engaging end axial view of the locking cam of FIG. 22;

FIG. 27 is a perspective view of a connector according to an alternative embodiment of the invention;

FIG. 28 is a top plan view of the connector shown in FIG. 27;

FIG. 29 is a side elevation view of the connector shown in FIG. 27;

FIG. 30 is an end elevation view of the connector shown in FIG. 27;

FIG. 31 is a perspective view of an extending shaft according to an embodiment of the invention shown with a fixed jaw fitting;

FIG. 32 is a side elevation view of the extending shaft of FIG. 31;

FIG. 33 is a top view of the extending shaft of FIG. 31;

FIG. 34 is a side elevation cutaway view of the extending shaft shown in FIG. 32;

FIG. 43 is a perspective view of a retaining ring according to an embodiment of the invention;

FIG. 44 is an end elevation view of the retaining ring shown in FIG. 43;

FIG. 45 is a perspective view of a connector according to an alternative embodiment wherein the housing and the extending shaft are bent;

FIG. 46 is a front elevation view of the connector shown in FIG. 45;

FIG. 50 is a partial perspective view of an alternative embodiment of the invention wherein the extending shaft has circumferential grooves, shown in an unlocked position;

FIG. 51 is a side elevation view of the connector shown in FIG. 50;

FIG. 52 is a partial perspective view of the connector shown in FIG. 50, shown in a locked position;

FIG. 53 is a side elevation view of the connector shown in FIG. 52;

FIG. 58 is a perspective view of an alternative embodiment of the invention utilizing a portion of the housing to articulate;

FIG. 59 is a side elevation view of the connector shown in FIG. 58;

FIG. 60 is a top view of the connector shown in FIG. 58;

FIG. 64 is a partial perspective view of an alternative embodiment of the invention utilizing a helical ratcheting extending shaft, shown in an unlocked position;

FIG. 65 is a side elevation view of the connector shown in FIG. 64;

FIG. 66 is a partial perspective view of the connector shown in FIG. 64, but shown in a locked position;

FIG. 67 is a side elevation view of the connector shown in FIG. 66;

DETAILED DESCRIPTION OF THE PREFERRED EMBODIMENT

While the present invention will be described more fully hereinafter with reference to the accompanying drawings, in which particular embodiments and methods are shown, it is to be understood from the outset that persons of ordinary skill in the art may modify the invention herein described while achieving the functions and results of this invention. Accordingly, the description that follows is to be understood as illustrative and exemplary of specific embodiments within the broad scope of the present invention and not as limiting the scope of the invention. In the following descriptions, like numbers refer to similar features or like elements throughout. As stated before, the invention is usable in a variety of medical applications and indeed is not limited to spinal applications. The invention will be denoted as connector 10, it being understood that a variety of implant locations are possible.

For ease of understanding, however, since spinal applications currently see great benefit from the invention, the following description is made with reference to spinal applications.

Figure 1:
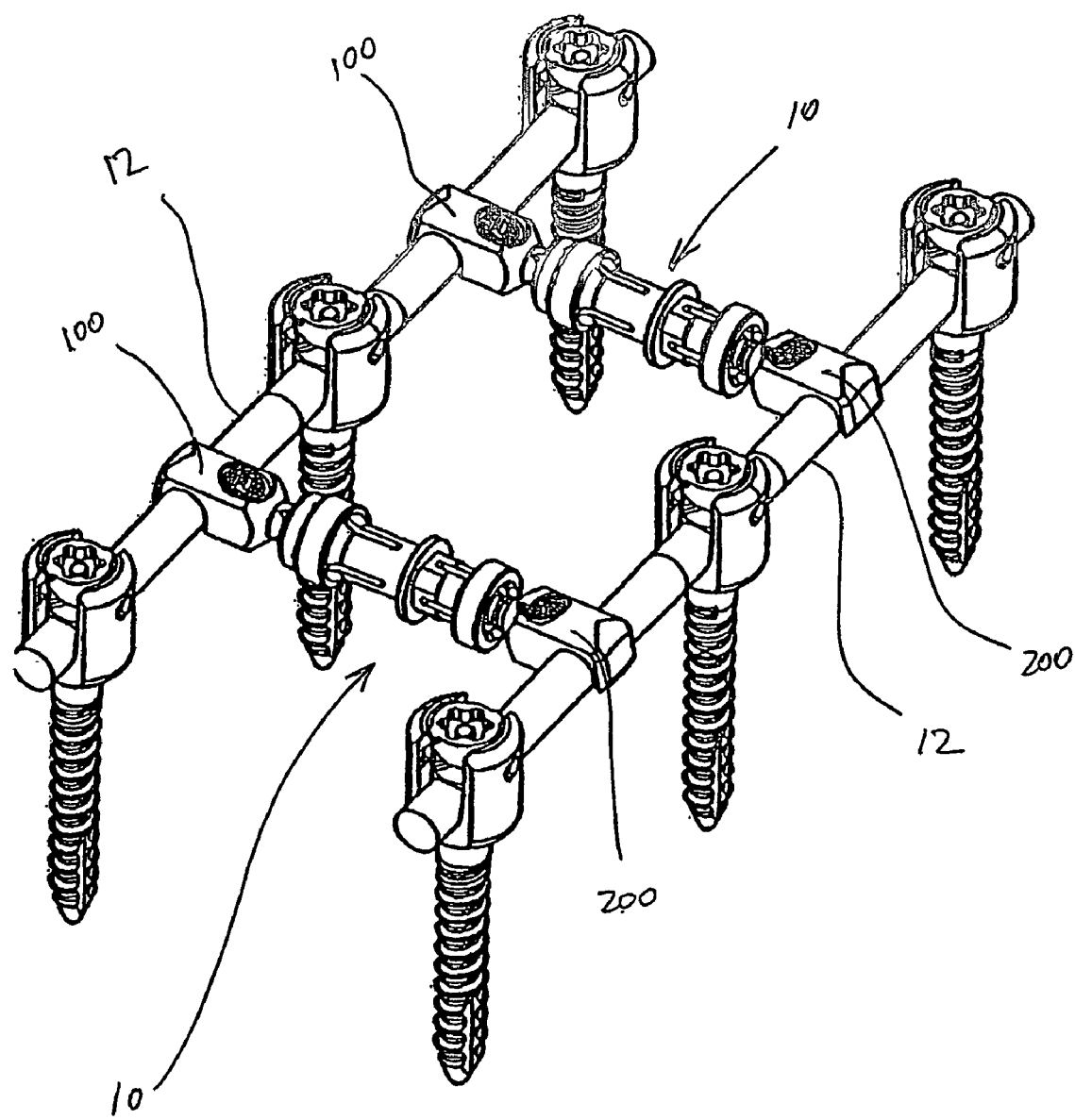
FIG. 1 is a perspective view of the apparatus according to one embodiment showing two connectors of the invention being used to connect two surgical rods secured to multiple bone anchors.
Figure 2:
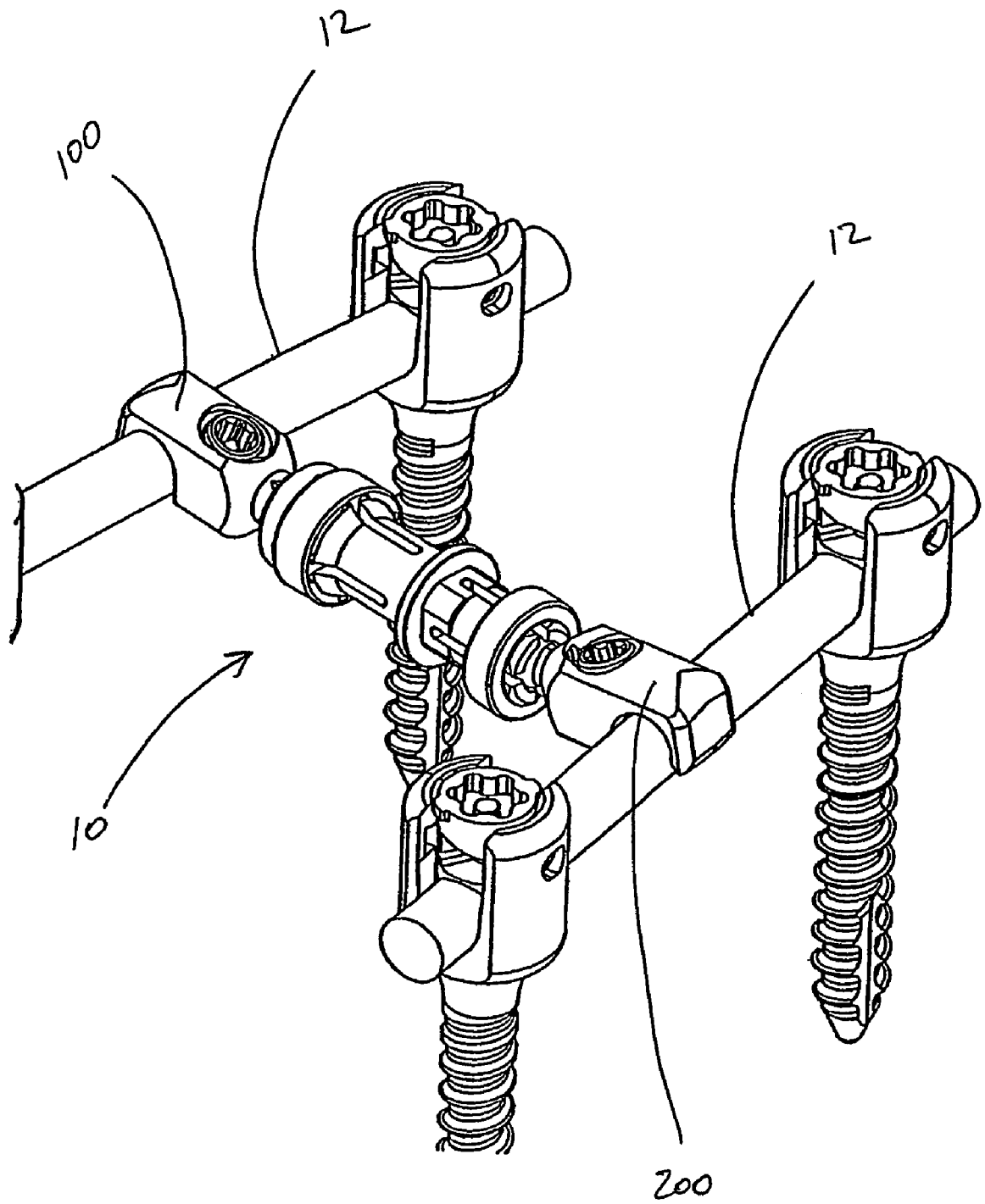
FIG. 2 is a close-up perspective of a connector according to one embodiment wherein the connector further comprises an articulating jaw that is securing two non-parallel surgical rods.
Figure 6:
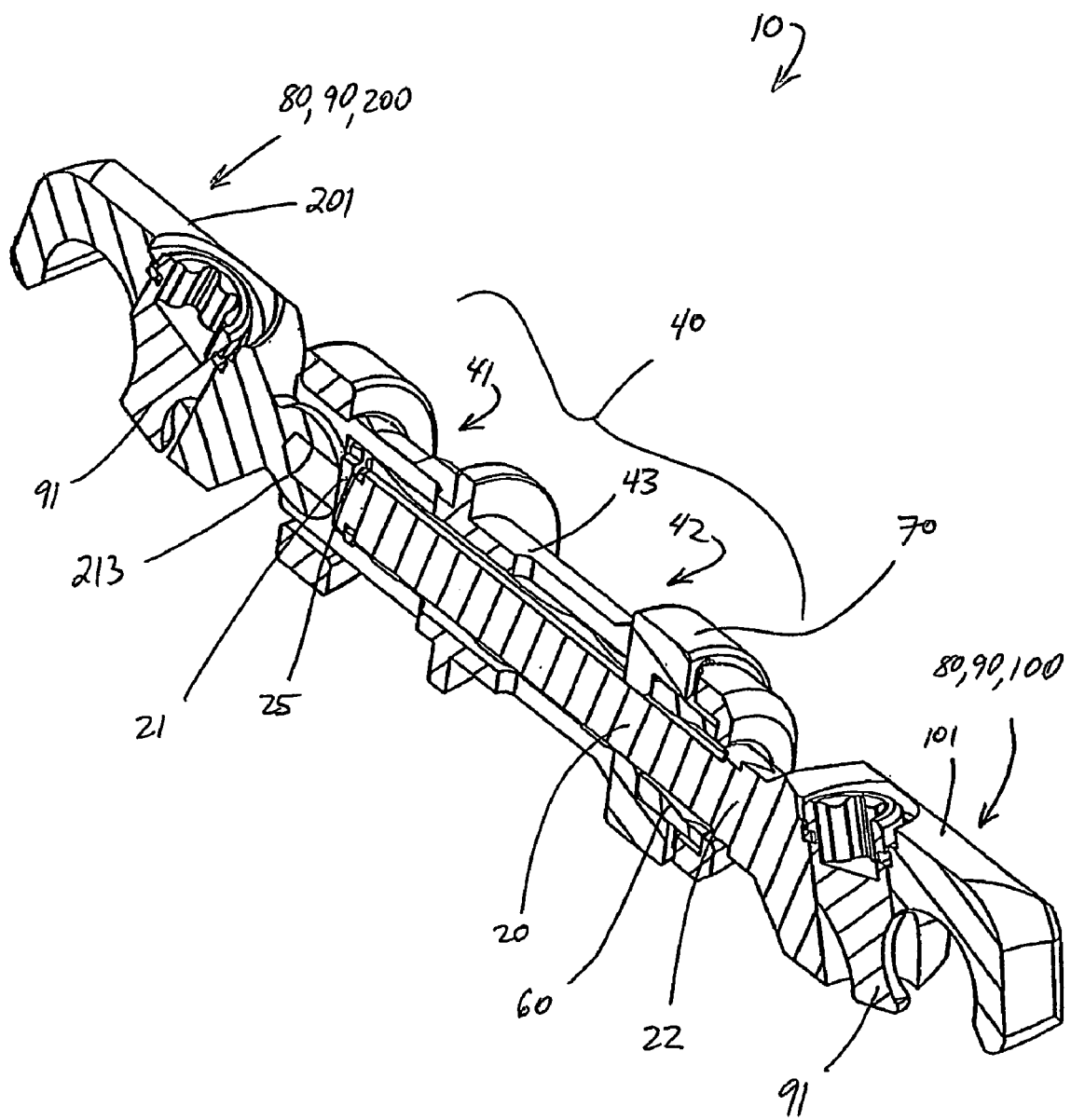
FIG. 6 is a section view in perspective of the connector according to an embodiment of the invention having a fixed jaw and an articulating jaw.
Figure 15:
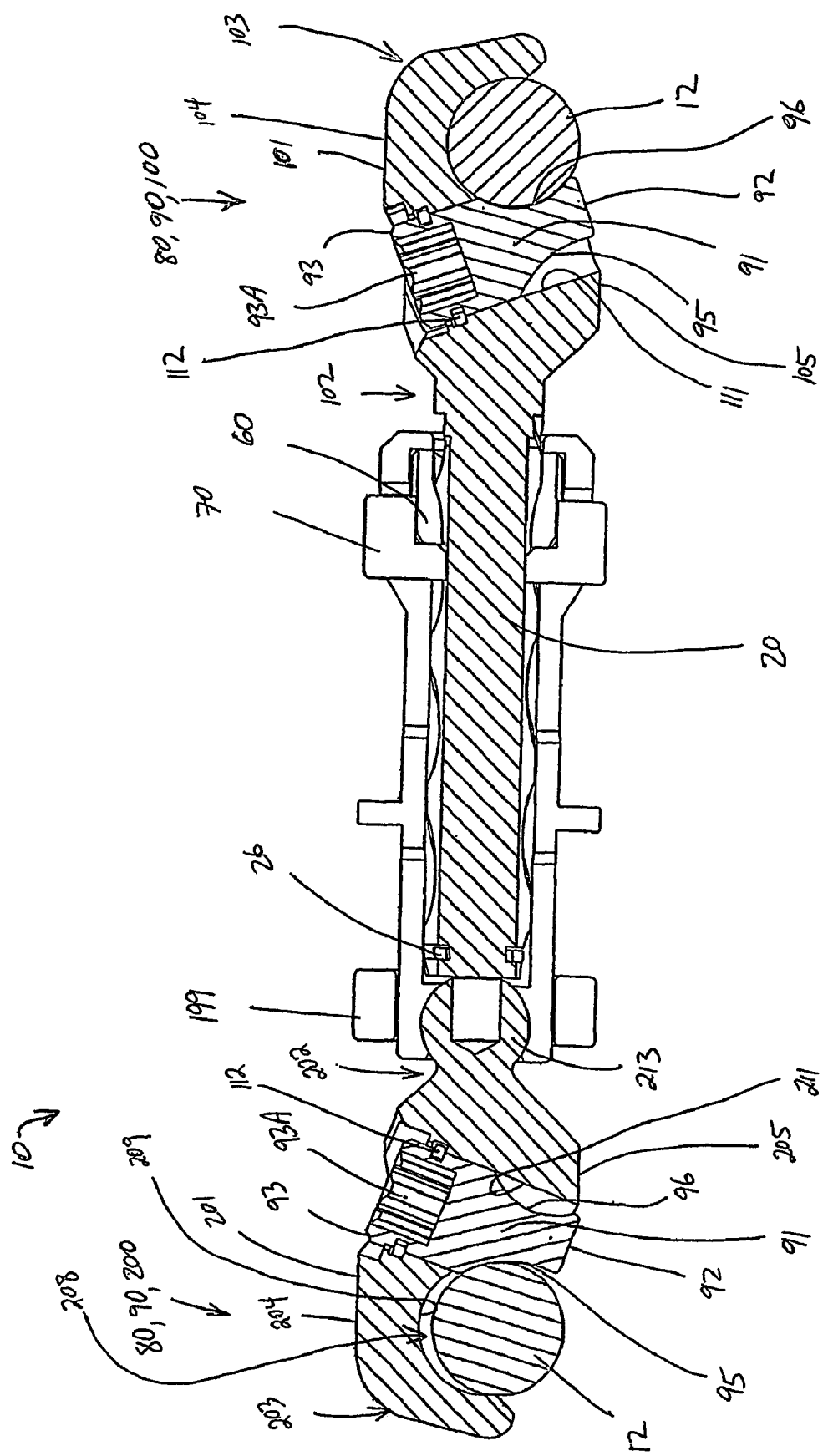
FIG. 15 is a sectional elevation view of a connector according to the invention having a fixed jaw (shown with a rod in the jaw and the cam in a locked position) and an articulating jaw (shown with the rod in the jaw and the cam in an unlocked position)
Figure 19:
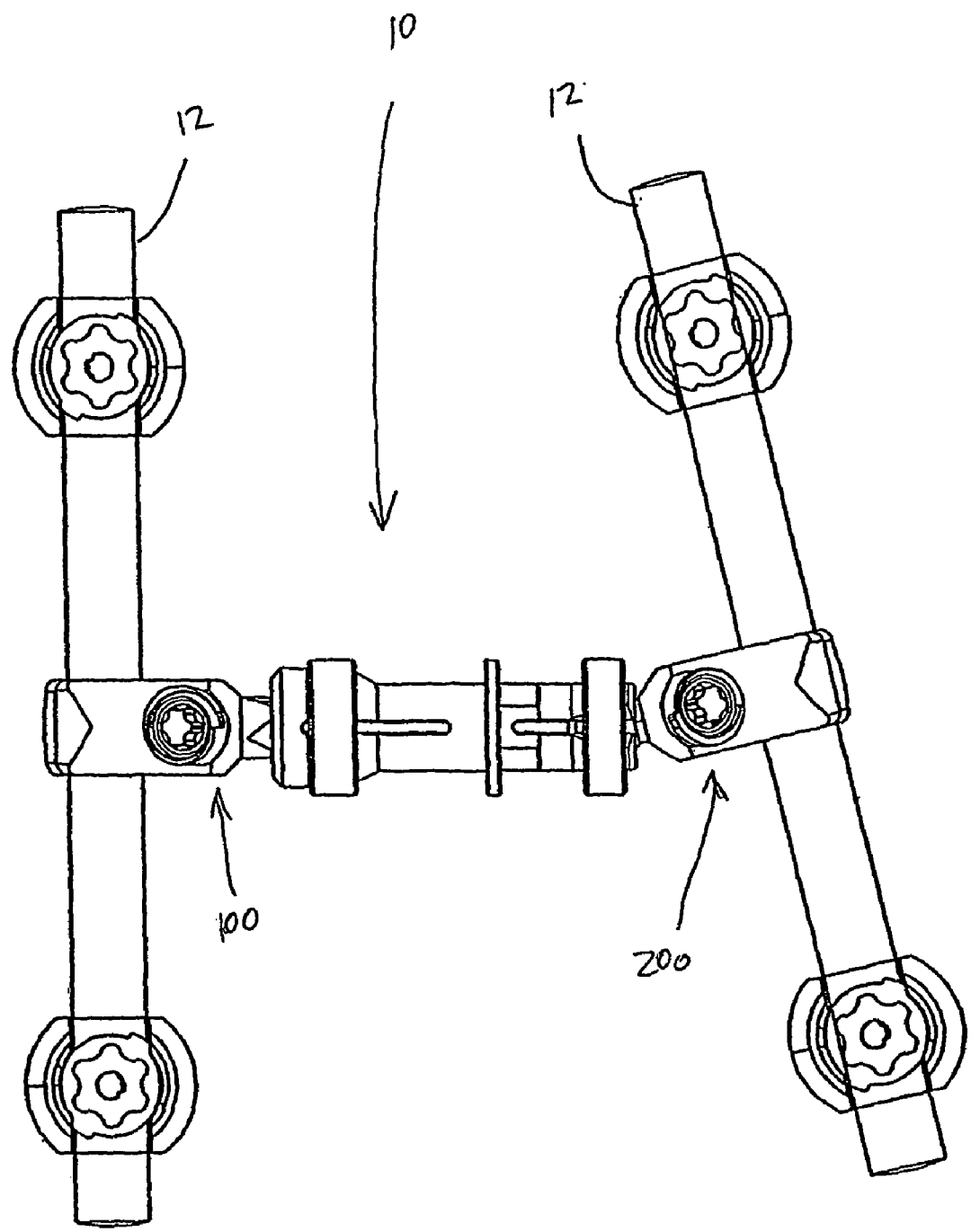
FIG. 19 is a top plan view of the connector shown in FIG. 2.
Figure 20:
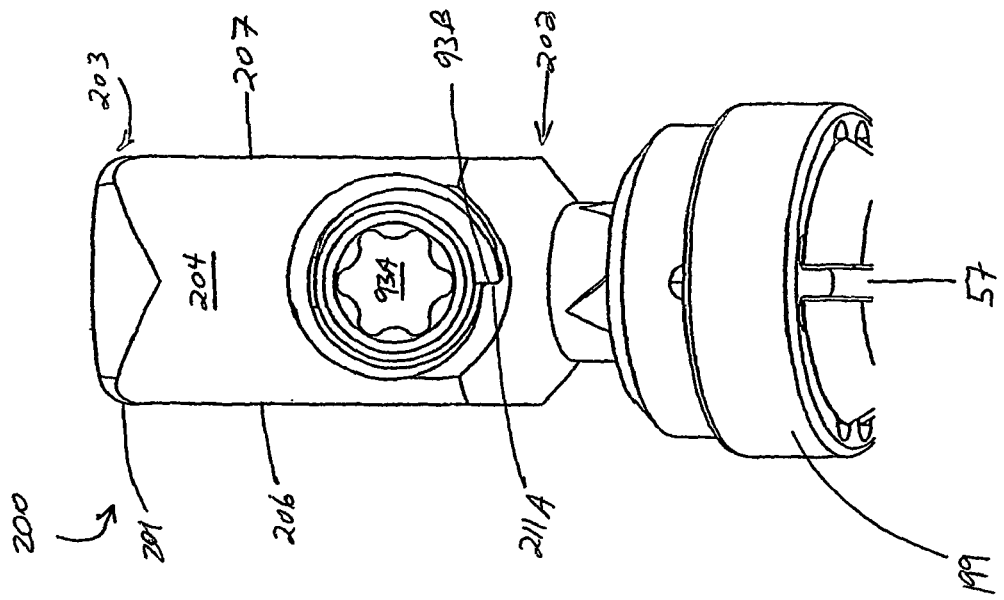
FIG. 20 is a partial top plan view of an articulating jaw of a connector according to one embodiment of the invention showing the locking cam in a locked positions and the articulating jaw in an unlocked position.
Figure 21:
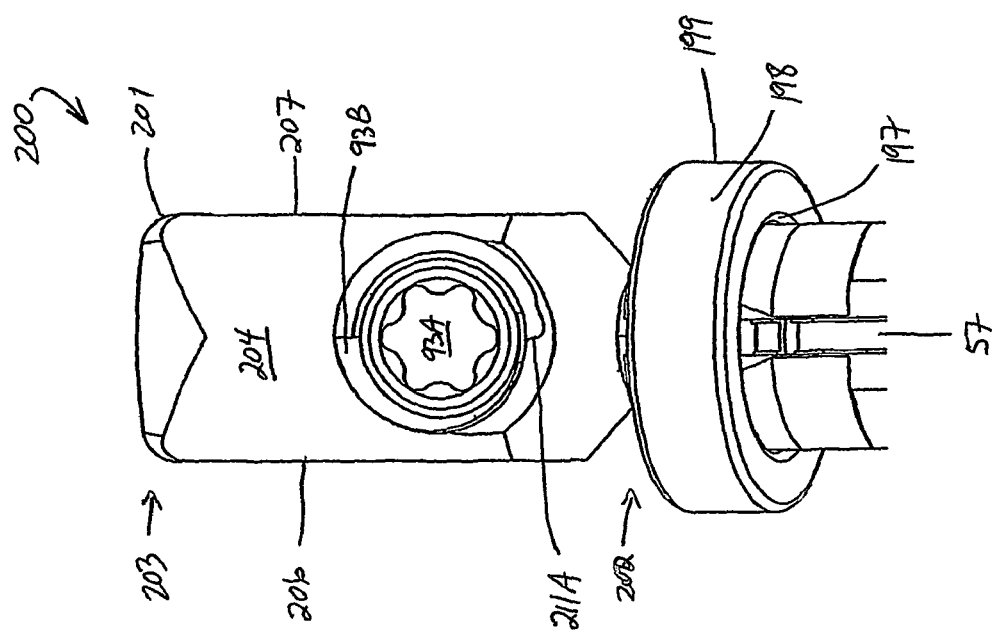
FIG. 21 is partial top plan view of the articulating jaw shown in FIG. 20 showing the locking cam in an unlocked position and the articulating jaw in a locked position.
Figure 35:
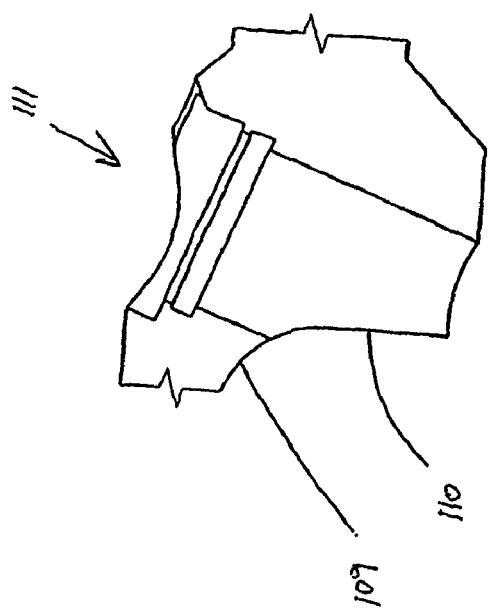
FIG. 35 is an enlarged cutaway view of the radial opening and the axial opening of the body of a fixed jaw shown in FIG. 34.
Figure 36:
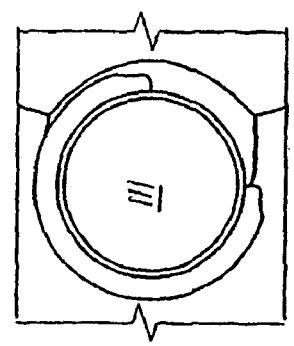
FIG. 36 is a top view of the radial opening shown in FIG. 35.
Figure 40:
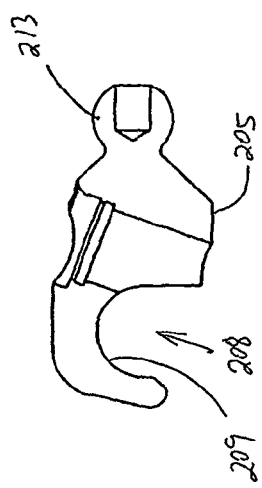
FIG. 40 is a side elevation cutaway view of the articulating jaw shown in FIG. 38.
Figure 39:
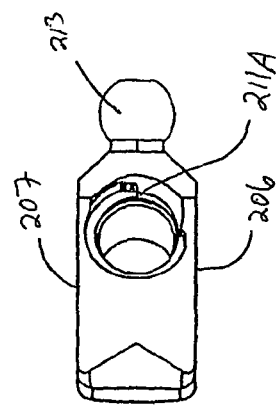
FIG. 39 is a top view of the articulating jaw shown in FIG. 37.
Figure 38:
FIG. 38 is a side elevation view of the articulating jaw shown in FIG. 37.
Figure 41:
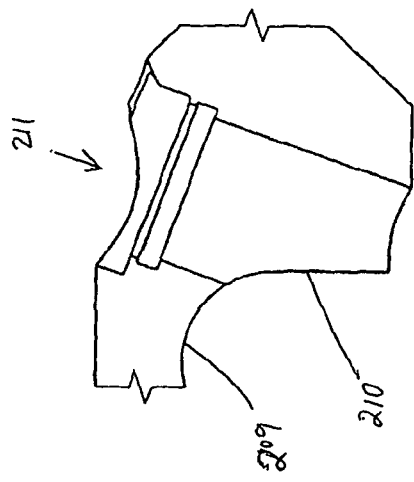
FIG. 41 is an enlarged cutaway view of the radial opening and the axial opening of the body of the articulating jaw shown in FIG. 40.
Figure 42:
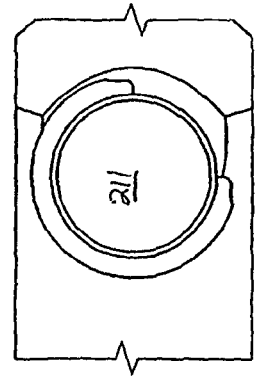
FIG. 42 is a top view of the radial opening shown in FIG. 41.
Figure 37:
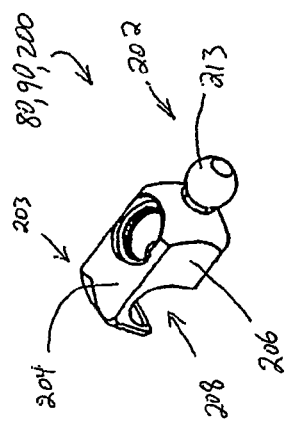
FIG. 37 is a perspective view of an articulating jaw according to an embodiment of the invention.

FIGS. 1, 2, and 19 show connectors 10 according to an embodiment of the invention in use as connectors to secure and connect two spinal rods 12. The connectors 10 can have fixed jaws 100, articulating jaws 200, or a combination of fixed and articulating jaws. The connectors 10 can thus accommodate rods 12 in any orientation and spatial arrangement.

FIGS. 3-6 show additional views of a connector 10 according to an embodiment of the invention. The connector 10 generally comprises a two-piece body having an extending shaft 20 and a housing 40; a rotor 60; and a locking collar 70. Each end of the connector 10 has a fitting 80 for engaging a structure (e.g., a rod 12, a vertebral body, and the like). In embodiments wherein the connector 10 is used to connect rods 12, the preferable fittings 80 comprise jaws 90 for engaging the rod 12. The jaws 90 can be in the form of a fixed jaw 100 or an articulating jaw 200, depending on the needs of the surgeon. Each fitting 80 includes a proximal end 81 and a distal end 82. The proximal end 81 preferably engages the connector 10 while the distal end 82 preferably engages other structures (for example, rods 12 in some embodiments or vertebral bodies in other embodiments, to name just a couple).

FIGS. 7-10 show a housing 40 of an adjustable embodiment for use with an articulating jaw 200. The housing 40 has a first portion 41 and a second portion 42 and preferably comprises two parts: a body 43 and a rotor 60. The first portion 41 preferably is attachable to an articulating jaw 200 (described below). The second portion 42 receives the extending shaft 20 (described below). The housing 40 is generally cylindrical with a first axial opening 44 therein for receiving the articulating jaw 200 and a second axial opening 45 therein for receiving the extending shaft 20. The rotor 60 is located in the second axial opening 45. The rotor 60 is generally cylindrical having an outer surface 61 and an inner surface 62. The inner surface 62 preferably contains one or more helical grooves 63 thereon so as to mate with corresponding helical grooves of the extending shaft 20. The outer surface 61 preferably contains circumferential grooves 64.

The second portion 42 preferably has a generally stepped cylindrical shape with a proximal end 46 having a first outer surface 48 and a distal end 47 having a second outer surface 49, wherein the second outer surface 49 has a diameter greater than that of the first outer surface 48. One or more slots 50 are formed in the first and second outer surfaces 48, 49. A ramping surface 51 provides a transition between the first outer surface 48 and the second outer surface 49. A lip 52 preferably is provided at the distal end of the ramping surface 51.

Referring to FIGS. 31-36, a typical extending shaft 20 is depicted. These figures show a fixed jaw 100 attached as the fitting 80, but recall that many types of fittings 80 are possible, including articulating jaws 200 (when used to connect rods 12) or other forms of endplates and so forth (when used as a corpectomy device). The extending shaft 20 has a first end 21 and a second end 22 wherein the first end 21 is insertable into the second axial opening 45 of the second portion 42 and wherein the second end 22 is typically fitted with fitting 80. The extending shaft 20 has one or more helical grooves 23 disposed about its outer surface 24. A groove 25 is preferably located near the first end 21. This groove 25 will receive a retaining ring 26 (see FIGS. 43-44) which has a leading surface 27 and a trailing surface 28 and an inner diameter 29 and an outer diameter 30. As with many retaining rings, retaining ring 26 is resiliently expandable (such that inner diameter 29 and outer diameter 30 increase) so as to be fitted over the extending shaft 20 and moved to its residence in the groove 25, whereupon it contracts to its equilibrium dimensions. Similarly, the retaining ring 26 is resiliently contractible (such that inner diameter 29 and outer diameter 30 decrease) so as to be forcibly inserted into the second axial opening 45 past a structure that has an opening smaller than the outer diameter 30 (which could be a structure within the second portion 42 or which could be the inner surface 72 of the locking collar 70 (described below), as but two examples).

Figure 16:
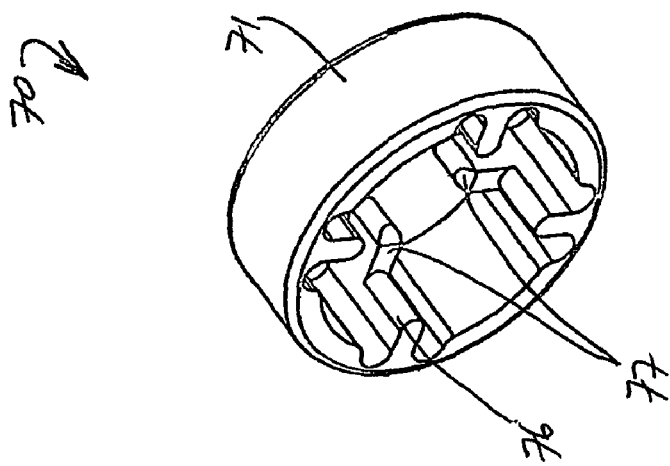
FIG. 16 is a perspective view of a locking collar according to an embodiment of the invention.
Figure 18:
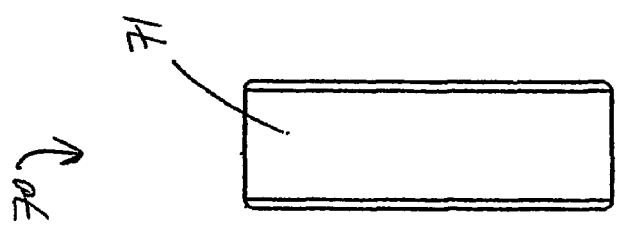
FIG. 18 is a side elevation view of the locking collar shown in FIG. 16.
Figure 17:
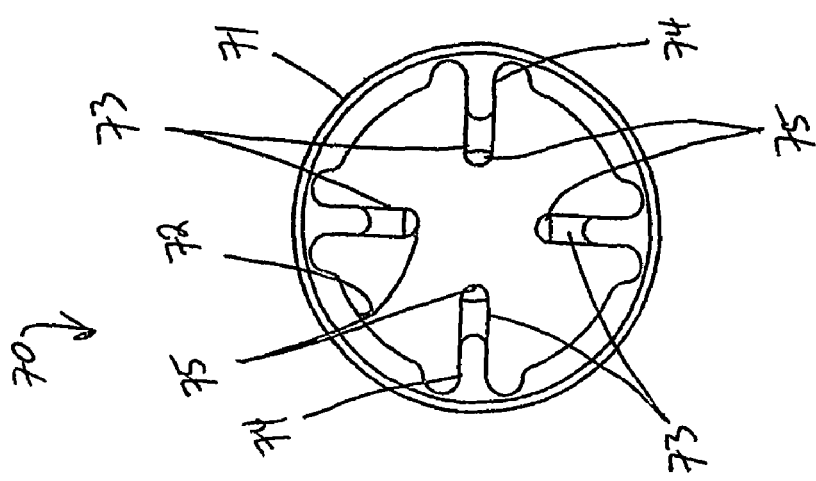
FIG. 17 is an end view of the locking collar shown in FIG. 16.

Referring to FIGS. 16-18, surrounding the body 43 is preferably a locking collar 70. The locking collar 70 is generally cylindrical in shape and comprises an outer surface 71 and an inner surface 72 and a proximal end 74 and a distal end 75. One or more protrusions 73 extend inwardly from the inner surface 72. The protrusions 73 are preferably stepped such that they have a first height 76 at the proximal end 74 and a second height 77 at the distal end 75, wherein the second height 77 is greater than the first height 76. The protrusions 73 reside in the slots 50, thus locating the locking collar 70 on the second portion 42 of the body 43. The locking collar 70 is slideable between a first unlocked position and a second locked position. In the first unlocked position, the locking collar 70 is located toward the proximal end 46 on the first outer surface 48 and the protrusions 73 do not engage the circumferential grooves 64 of the rotor 60. As the locking collar 70 is slid toward the distal end 47, the inner surface 72 of the locking collar 70 begins contacting the ramping surface 51. In the lock position the locking collar 70 passes over lip 52 and the inner surface 72 contacts the second outer surface 49. In this position, the second height 77 of the protrusions 73 engages one or more circumferential grooves 64 on the outer surface 61 of the rotor 60. In this position, the protrusions 73 prevent the rotor 60 from rotating about its axis.

With continuing reference to FIGS. 31-36, the fitting 80 is shown in this embodiment as a fixed jaw 100. The fixed jaw 100 shown here comprises a body 101 having a proximal end 102 and a distal end 103; an upper surface 104 and a lower surface 105; and a first side surface 106 and a second side surface 107. In the embodiment shown for connecting rods 12, a rod opening 108 extends through the first and second side surfaces 106, 107 and is preferably open at the lower surface 105. The rod opening 108 forms an inner surface 109 that forms a partial cylindrical shape. The inner surface 109 has an axial opening 110 near the proximal end 102 for communication with a locking cam 90 (described below). The locking cam 90 is insertable in a radial opening 111 preferably located in the upper surface 104. The locking cam 90 is preferably retained in the radial opening 111 by a retaining ring 112 with structure and function similar to that of retaining ring 26.

Referring now to FIGS. 7-10 and 15, the first portion 41 is shown as attachable to a fitting 80 that takes the form of an articulating jaw 200. The first portion 41 preferably has a generally stepped open cylindrical shape with a proximal end 53 having a first outer surface 55 and a distal end 54 having a second outer surface 56, wherein the second outer surface 56 has a diameter greater than that of the first outer surface 55. Grooves 57 are formed in the distal end 54 at the first axial opening 44 so as to create resilient fingers 58. The resilient fingers 58 have an entrance diameter 58A and an internal opening 58B having a diameter 58C located a distance within the first portion 41, wherein the diameter 58C is greater than the entrance diameter 58A. A ramping surface 59 provides a transition between the first outer surface 55 and the second outer surface 56. A collar 199 having a generally open cylindrical shape has an outer surface 198 and an inner surface 197 and is assembled first to reside about the first outer surface 55 in an unlocked position. The collar 199 is slideable distally from the unlocked position to a locked position wherein the inner surface 197 surrounds the second outer surface 56. In this position, since the second outer surface 56 has a diameter greater than the first outer surface 55, the inner surface 197 of the locking collar 199, as it moves along ramping surface 59 and into the locking position, forces resilient fingers 58 to deflect inwardly. When a ball 213 (described below) is present within the internal opening 58B, this deflection locks the fingers 58 onto the outer surface of the ball 213, thus maintaining the articulating jaw 200 in a desired orientation.

Referring to FIGS. 37-42, a particular articulating jaw 200 is shown. The articulating jaw 200 has many of the same structures as that of the fixed jaw 100, and so the similar features will not be further described. These similar features include a body 201 having a proximal end 202 and a distal end 203; an upper surface 204 and a lower surface 205; a first side surface 206 and a second side surface 207; a rod opening 208; inner surface 209; axial opening 210; radial opening 211; and retaining ring 212. Additionally, however, the articulating jaw 200 further comprises a ball 213 located at the proximal end 202. The ball 213 can take several shapes, including spherical and ovoidal, but is preferably spherical. The ball 213 has a diameter 214 that is preferably larger than the entrance diameter 58A and less than or equal to the diameter 58C.

Referring now to FIGS. 3, 4, 6, and 22-26, each jaw 90, whether fixed or articulating, preferably has a locking cam 91 for alternately engaging or disengaging a rod 12 therein. A particularly useful embodiment of a locking cam 91 is shown in FIGS. 22-26, though many other types of connectors or cams can be used. The locking cam 91 generally comprises an engaging end 92 and a driving end 93, wherein the engaging end 92 is fitted with a complex curvate surface 94 having at least a first curvate surface 95 and a second curvate surface 96 such that in an unlocked position, the rod 12 can slide freely within the jaw 90, and in a locked position, the rod 12 is securely locked to the jaw 90 of the connector 10. The locking cam 91 can have a retaining mechanism 97 to keep the locking cam 91 in the jaw 90, such as a retaining ring that snaps into an undercut 98 in the jaw 90. Many embodiments of the engaging end of the locking cam 91 are possible to accomplish this. The embodiment shown in FIG. 15 utilizes a complex curvature such that in section view—in an unlocked position (see the left jaw 90)—the first curvate surface 95 is located adjacent the rod 12, and the second curvate surface 96 is located away from the rod 12. The first curvate surface 95 may have a radius of curvature that is greater than that of the second curvate surface 96. Alternatively, the first curvate surface 95 may have the same radius of curvature as that of the second curvate surface 96 but may offset the origin of the curvature farther away from the centerline of the locking cam 91. Upon rotation of the locking cam 91 from the unlocked to the locked position (see the right jaw 91 shown in FIG. 15), gradually the second curvate surface 96 is brought into contact with the rod 12, which wedges the rod 12 against the inner surface 109 within the jaw 90, thereby locking the rod 12 in position. This ability to draw the rod 12 up to the jaw 90 compensates for any misalignment between the opposing rods 12.

FIGS. 20-26 and 37-42 show one example of the visual and tactile feedback provided by the locking cams 91 of the invention on use with an articulating jaw 200. As stated above, the locking cam 91 generally comprises an engaging end 92 and a driving end 93. The driving end 93 is preferably circular in cross section and has a cavity 93A to receive a driving instrument (not shown) and an appurtenant stop 93B disposed at a location along its perimeter. The locking cam 91 is inserted into the radial opening 211 and is secured therein by a retaining mechanism 97. The radial opening 211 preferably comprises a substantially circular opening having a discontinuity 211A disposed out of phase with the appurtenant stop 93B when in the unlocked position. A driving instrument turns the locking cam 91 the desired amount (preferably approximately 180 degrees). This turning rotates the engaging end 92 about the locking cam's 91 axis of rotation, which brings the second curvate surface 96 into contact with the rod 12, which wedges the rod 12 against the inner surface 209. When fully turned, the appurtenant stop 93B engages the discontinuity 211A, which visually and tactilely informs the surgeon that the cam is locked.

FIGS. 27-30 show an alternative embodiment of a connector 10 of fixed length. Various sizes of such connectors 10 can be manufactured according to common lengths needed for patients of varying sizes and varying portions of the spine. In this embodiment, although no length adjusting mechanism as described above is present, the novel locking cam 91 structure to secure the rods 12 is present.

FIGS. 45 and 46 show an alternative embodiment of a connector 10 wherein the extending shaft 20 and the housing 40 are pre-bent to account for spinal curvature. Such embodiment can better reduce or eliminate interference of the connector 10 with vertebrae or other structures.

Figure 47:
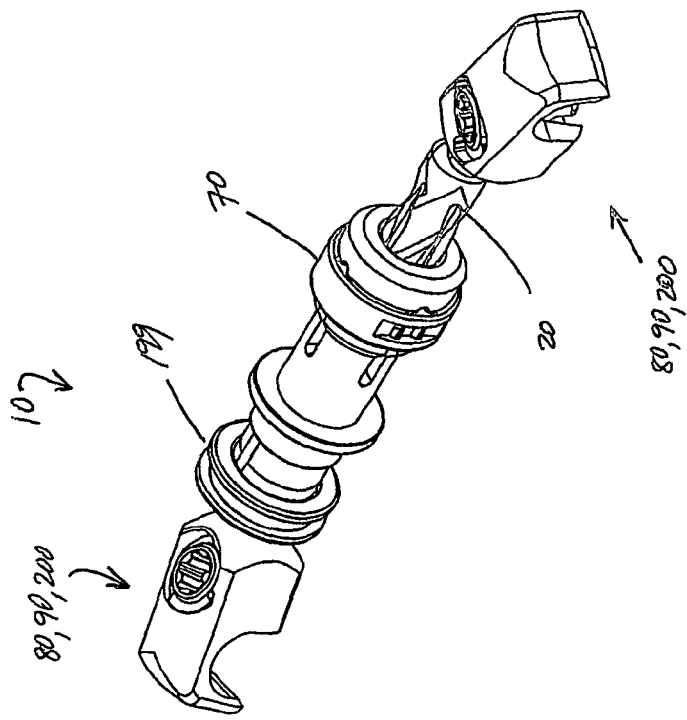
FIG. 47 is a perspective view of a connector according to an alternative embodiment wherein the connector incorporates two articulating jaws.
Figure 48:
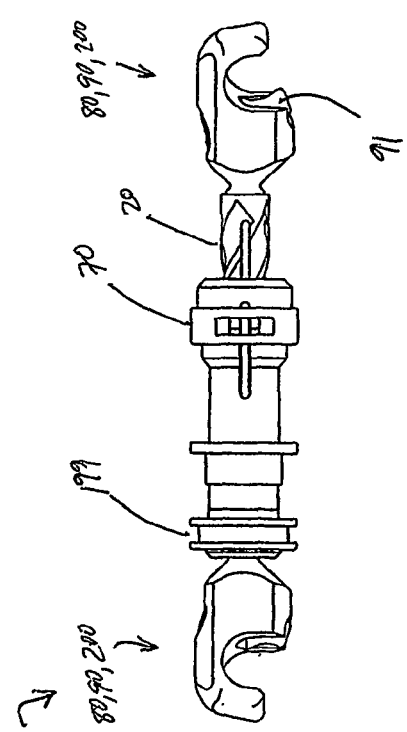
FIG. 48 is a front elevation view of the connector shown in FIG. 47.
Figure 49:
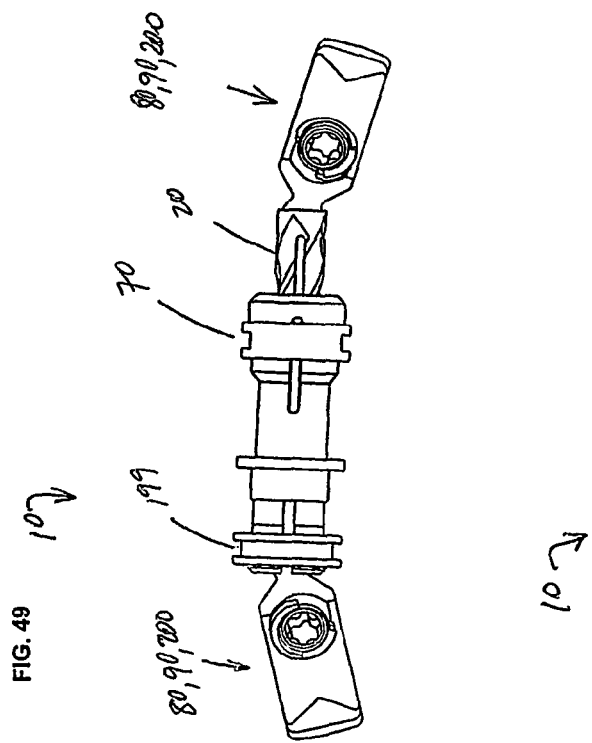
FIG. 49 is a top view of the connector shown in FIG. 47.
Figure 54:
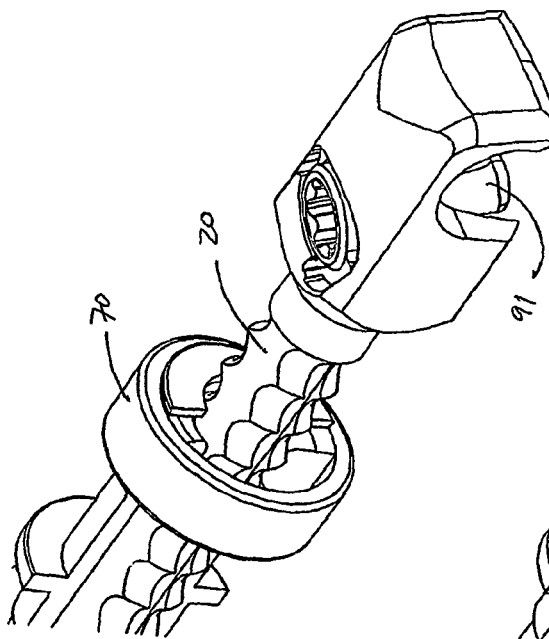
FIG. 54 is a partial perspective view of an alternative embodiment of the invention wherein the extending shaft has circumferential grooves but the shaft directly interfaces the locking collar, shown in an unlocked position.
Figure 56:
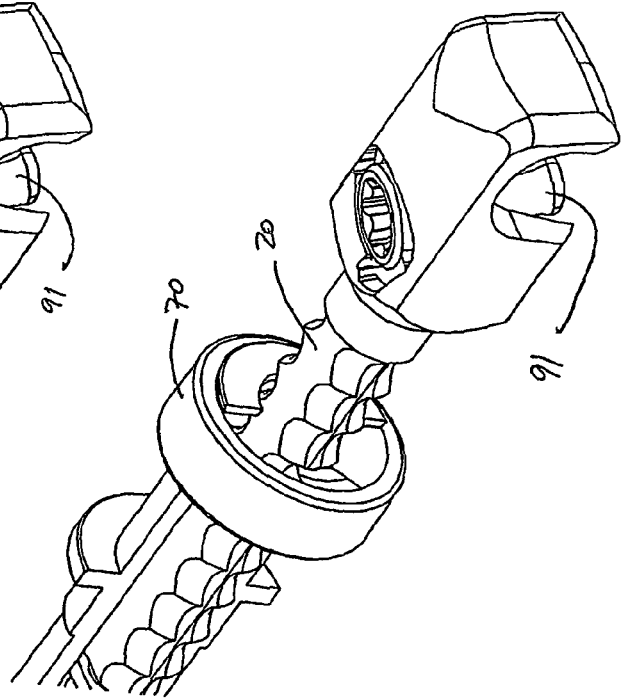
FIG. 56 is a perspective view of the connector shown in FIG. 54, shown in a locked position.
Figure 55:
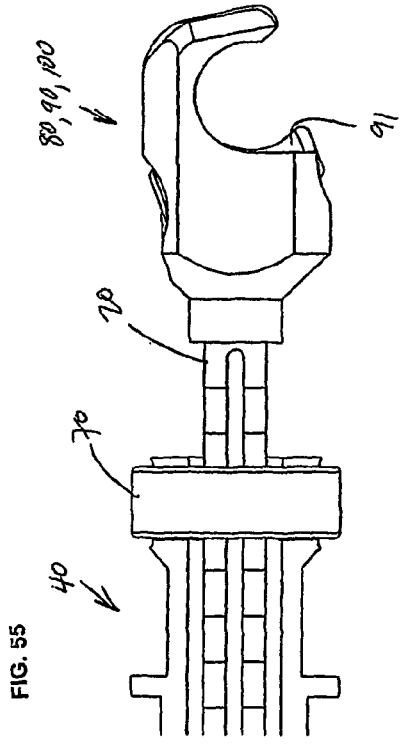
FIG. 55 is a side elevation view of the connector shown in FIG. 54.
Figure 57:
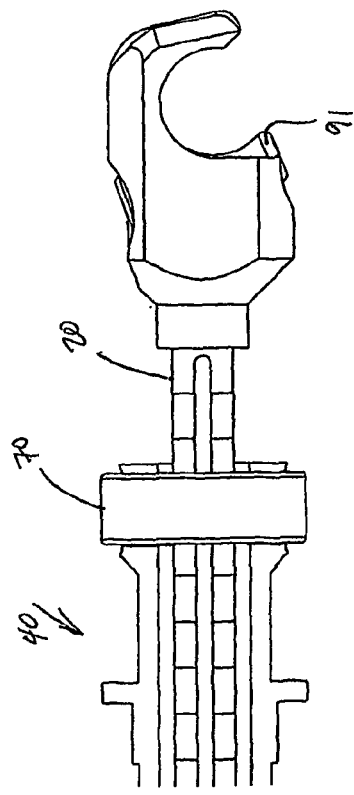
FIG. 57 is a side elevation view of the connector shown in FIG. 56.

FIGS. 47-49 show an alternative embodiment of a connector 10 wherein the connector 10 contains two articulating jaws 200. Such embodiment is useful where the rods 12 are highly divergent. Without multiple articulating jaws 200, bending may be required for some connectors 10. This embodiment employs an articulating jaw 200 on both ends of the connector 10 to eliminate the need for any bending. It also enables better placement of the connector in vivo to avoid any interference from surrounding structures. The articulating jaw in the extending shaft 20 is similar in structure and function to that of the already described articulating jaw 200, providing means for rotating the jaw; locking it to the extending shaft 20; and telescoping the extending shaft 20 out of the housing 40.

FIGS 50-53 show an alternative embodiment of a connector 10 wherein the extending shaft 20 comprises circumferential grooves 23A along the length thereof. The housing 40 has a corresponding ring 45A with grooves, for example within second axial opening 45, that will mate with the grooves 23A on the extending shaft 20. The extending shaft 20 moves relative to the housing 40, thus varying the overall length of the connector 20. The ring 45A is deflectable such that once the extending shaft 20 is in the proper place the housing 40 can be locked down onto the extending shaft 20 via a locking collar 70. The locking collar 70 is located preferably around the end of the housing 40 and locks the housing 40 on the extending shaft 20 by means of a cam feature or similar devices.

FIGS. 54-57 show an alternative embodiment to the circumferential groove device. In this embodiment, the locking collar 70 directly interfaces the extending shaft 20. The locking collar 70 has circumferential grooves 23A on its inner diameter or portions thereof The locking collar 70 has an internal diameter that provides clearance to enable the extending shaft 20 to move axially relative to the housing 40. Conversely the extending shaft 20 has a portion thereof devoid of grooves to allow it to move freely relative to the locking collar 70. The locking collar 70 will be secured in place axially relative to the housing 40, but will be free to rotate a certain degree in order to interface with the extending shaft 20. When the desired length is reached the locking collar 70 can be turned a predetermined angle to engage the extending shaft 20. Other means of preventing the extending shaft 20 from rotating within the housing 40 are possible, including, but not limited to keys, pins, noncircular shaped second axial opening 45, and the like.

FIGS. 58-60 show an alternative embodiment of a connector 10 wherein instead of providing an articulating jaw 200, an articulating housing 40 is provided. Basically instead of employing the first axial opening 44 to receive the ball 213 of the articulating jaw 200, the first portion 41 of the housing 40 receives a ball. A locking mechanism can be incorporated into the connector 10 to permit the housing 40 to be fixed at a desired angle. The housing 40 preferably can pivot in all planes. Articulating jaws 200 as described above can be incorporated into this embodiment to allow for even more capability to interface with diverging rods.

Figure 61:
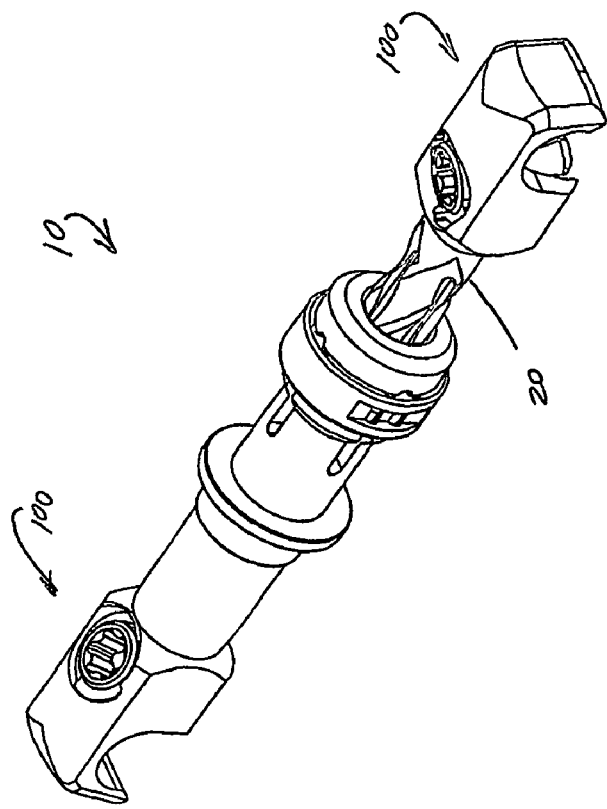
FIG. 61 is a perspective view of an alternative embodiment of the invention having two fixed jaws.
Figure 63:
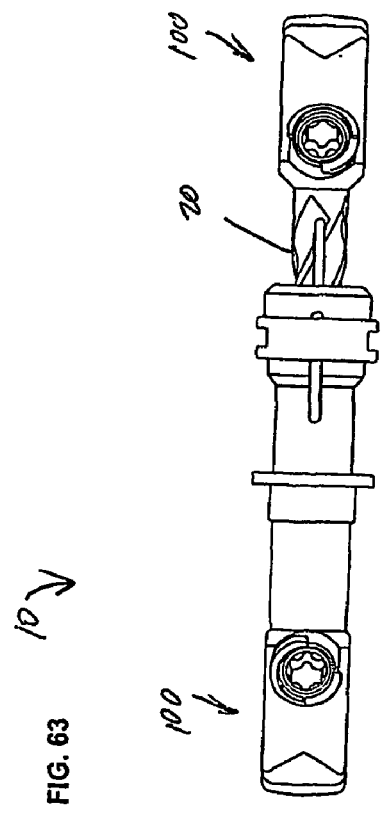
FIG. 63 is a top view of the connector shown in FIG. 61.
Figure 62:
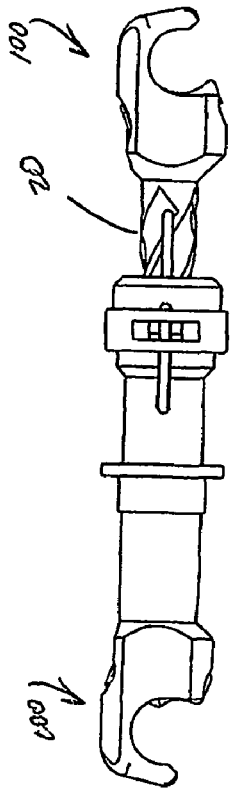
FIG. 62 is a side elevation view of the connector shown in FIG. 61.

FIGS. 61-63 show another alternative embodiment of a connector 10 wherein two fixed jaws 100 are in use. Any adjustments made to the connector to account for diverging rods 12 would have to be made by bending the connector 10 either at the extending shaft 20 or on the housing 40 itself. Bending could be made in any direction and would only be limited by the physical properties of the material.

FIGS. 64-67 show an alternative embodiment of a connector 10 having a ratcheting telescoping shaft 20. The shaft 20 contains helical grooves 23 similar to that previously described. The shaft 20 interfaces a rotor 60 that similarly has internal helical grooves 63 matching the external profile of the shaft 20. The rotor 60 likewise comprises circumferential grooves 64 or other indentations or extrusions on its external surface, again like that described above. A split ring 70A is provided that engages the circumferential grooves 64. The split ring 70A has engaging features on its internal surface which spring open when the circumferential grooves 64 rotate past them. This provides a ratcheting feel to the telescoping of the shaft 20. The advantage is that a shaft 20 can be placed at a predetermined length before implantation and then small adjustments and locking could be made in vivo. Locking is be accomplished by placing a ring, collar, or similar device onto the split ring 70A to prevent it from springing open. This in turn would prevent the rotor 60 from turning and the shaft 20 from translating.

Figure 68:
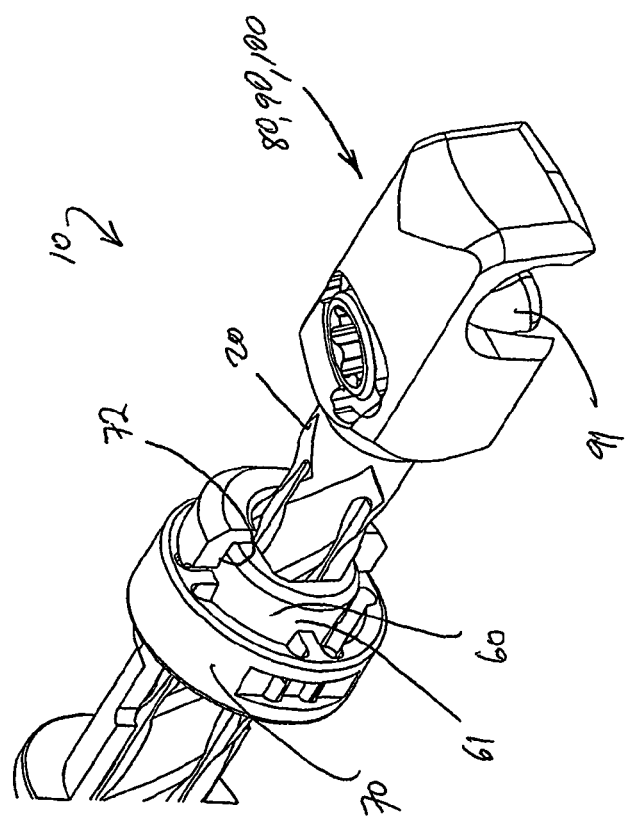
FIG. 68 is a partial perspective view of an alternative embodiment of the invention utilizing a taper lock.
Figure 69:
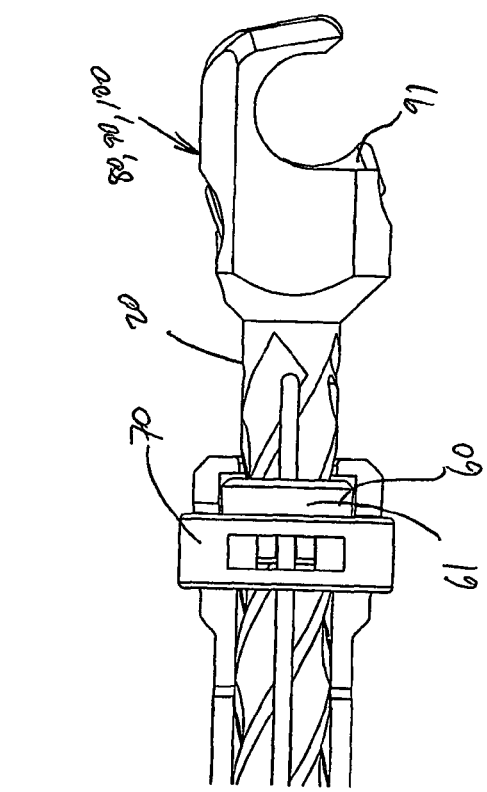
FIG. 69 is a side elevation view of the connector shown in FIG. 68.

FIGS. 68-69 show an alternative embodiment of a connector 10 utilizing a different means to lock the rotor 60. In this embodiment, a taper lock is used in place of the engaging features described above. The rotor 60 is cylindrical in shape but has a taper on the outer surface 61 in the direction of the rotational axis. A locking collar 70 has an inner surface 72 having a taper complementing that of the outer surface 61 of the rotor 60. The locking collar 70 resists rotation relative to the housing 40 thereby. Locking is accomplished by moving the locking collar 70 to interface the rotor 60 via the taper lock, thus preventing the rotor 60 from turning.

Figure 70:
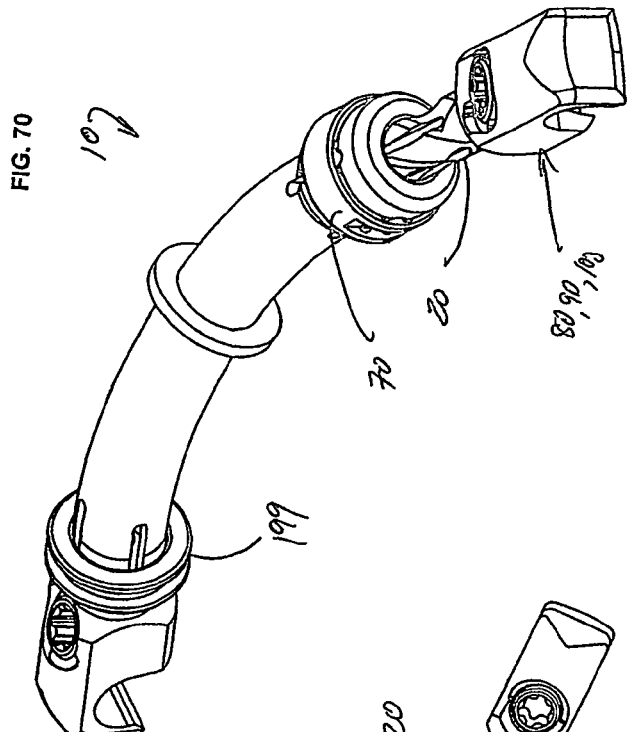
FIG. 70 is a perspective view of an alternative embodiment of the invention employing a housing bent in multiple planes.
Figure 72:
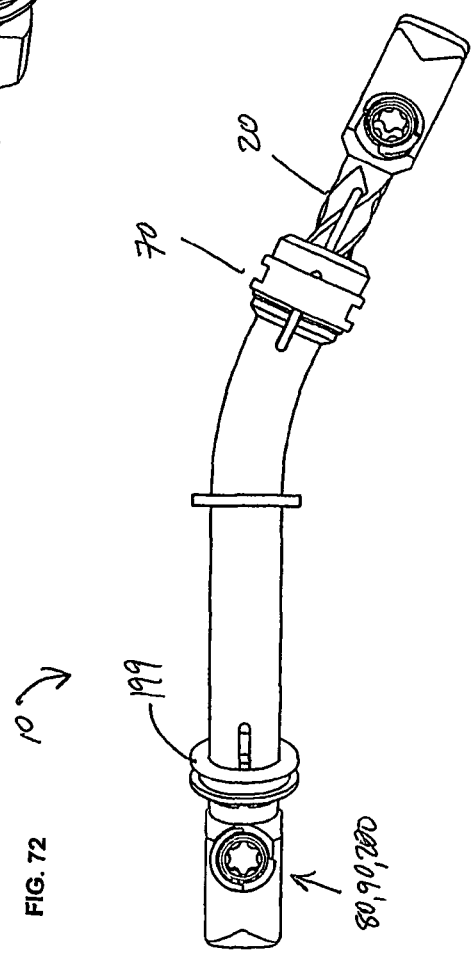
FIG. 72 is a top view of the connector shown in FIG. 70.
Figure 71:
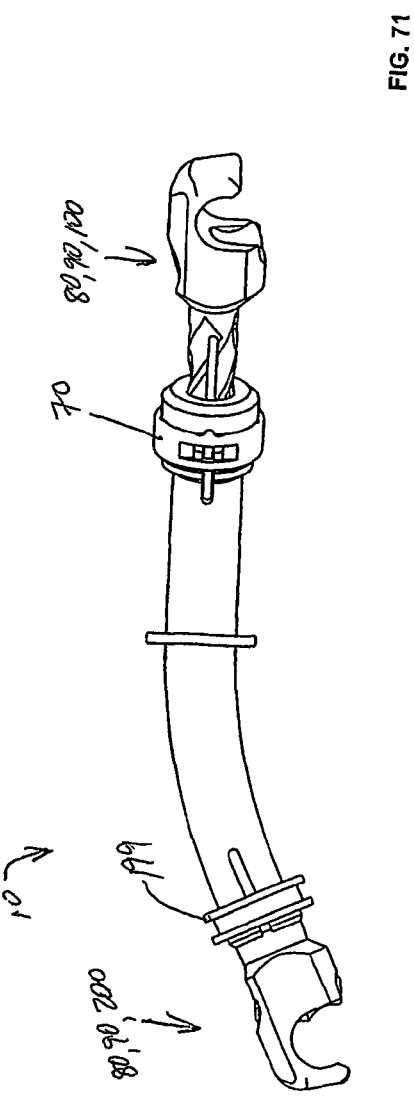
FIG. 71 is a side elevation view of the connector shown in FIG. 70.

FIGS. 70-72 show an alternative embodiment of a connector l that is pre-bent in multiple planes. Any combination of bends in planes parallel to the rods 12, perpendicular to the rods 12, or in planes between the two are possible. This would account for any misalignment and divergence of the rods 12. The connector 10 is intended to accommodate rods 12 that are divergent and at different heights. This embodiment is a variation of the embodiment shown in FIGS. 45 and 46.

While there has been described and illustrated particular embodiments of a novel adjustable implant device, it will be apparent to those skilled in the art that variations and modifications may be possible without deviating from the broad spirit and principle of the present invention, which shall be limited solely by the scope of the claims appended hereto.

What is claimed is:

1. An adjustable spinal implant comprising:
   an extending shaft having a proximal end and a distal end and having grooves on an external surface of said extending shaft;
   a first fitting attached to said distal end of said extending shaft for engaging a first structure;
   a substantially cylindrical housing having a proximal end and a distal end and an inner surface and an outer surface, wherein said proximal end of said housing receives therewithin said proximal end of said extending shaft;
   a substantially cylindrical rotor having an outer surface and an inner surface and having grooves on said inner surface engageable with said grooves on said extending shaft, wherein said rotor is axially fixed with respect to said housing;
   a locking collar disposed about said outer surface of said housing at said proximal end of said housing, wherein said locking collar comprises an outer surface and an inner surface and at least one protrusion directed radially inwardly for engagement with said outer surface of said substantially cylindrical rotor; and
   a second fitting attached to said distal end of said housing for engaging a second structure.

2. The adjustable spinal implant according to claim 1 wherein said grooves on said external surface of said extending shaft are helical.

3. The adjustable spinal implant according to claim 2 wherein said grooves on said inner surface of said rotor are helical and engage said grooves on said external surface of said extending shaft.

4. The adjustable spinal implant according to claim 3 wherein said rotor further comprises circumferential grooves disposed on said outer surface.

5. The adjustable spinal implant according to claim 4 wherein said at least one protrusion on said inner surface of said locking collar engages said circumferential grooves on said rotor.

6. The adjustable spinal implant according to claim 5 wherein said first fitting attached to said distal end of said extending shaft is a fixed jaw.

7. The adjustable spinal implant according to claim 6 wherein said fixed jaw is engageable with a first rod.

8. The adjustable spinal implant according to claim 7 wherein fixed jaw further comprises a proximal end and a distal end and an upper surface and a lower surface and a first side surface and a second side surface and a rod opening through said first and second side surfaces that is open at said lower surface, wherein said rod opening comprises a substantially cylindrical opening.

9. The adjustable spinal implant according to claim 8 wherein said fixed jaw further comprises an axial opening near said proximal end and a radial opening through said upper surface extending to said axial opening for receiving a locking device.

10. The adjustable spinal implant according to claim 9 wherein said locking device further comprises a cam having a generally cylindrical shape and a driving end and an engaging end.

11. The adjustable spinal implant according to claim 10 wherein said engaging end of said cam further comprises a first curvate surface corresponding to an unlocked cam position and a second curvate surface corresponding to a locked cam position.

12. The adjustable spinal implant according to claim 11 wherein said cam is rotatable from said unlocked position to said locked position whereupon said rotation alternately moves said first curvate surface away from said rod and moves said second curvate surface into engagement with said rod.

13. The adjustable spinal implant according to claim 12 wherein said second fitting attached to said distal end of said housing further comprises an articulating jaw engageable with a second rod.

14. The adjustable spinal implant according to claim 13 wherein articulating jaw further comprises a proximal end and a distal end and an upper surface and a lower surface and a first side surface and a second side surface and a rod opening through said first and second side surfaces that is open at said lower surface, wherein said rod opening comprises a substantially cylindrical opening.

15. The adjustable spinal implant according to claim 14 wherein said articulating jaw further comprises an axial opening near said proximal end in open communication with said rod opening and a radial opening through said upper surface extending to said axial opening for receiving a locking device.

16. The adjustable spinal implant according to claim 15 wherein said locking device further comprises a cam having a generally cylindrical shape and a driving end and an engaging end.

17. The adjustable spinal implant according to claim 16 wherein said engaging end of said cam further comprises a first curvate surface corresponding to an unlocked cam position and a second curvate surface corresponding to a locked cam position.

18. The adjustable spinal implant according to claim 17 wherein said cam is rotatable from said unlocked position to said locked position whereupon said rotation alternately moves said first curvate surface away from said rod and moves said second curvate surface into engagement with said rod through said axial opening.

19. The adjustable spinal implant according to claim 1 wherein said first fitting attached to said distal end of said extending shaft is a fixed jaw.

20. The adjustable spinal implant according to claim 19 wherein said fixed jaw is engageable with a first rod.

21. The adjustable spinal implant according to claim 20 wherein said fixed jaw further comprises a proximal end and a distal end and an upper surface and a lower surface and a first side surface and a second side surface and a rod opening through said first and second side surfaces that is open at said lower surface, wherein said rod opening comprises a substantially cylindrical opening.

22. The adjustable spinal implant according to claim 21 wherein said fixed jaw further comprises an axial opening near said proximal end in open communication with said rod opening and a radial opening through said upper surface extending to said axial opening for receiving a locking device.

23. The adjustable spinal implant according to claim 22 wherein said locking device further comprises a cam having a generally cylindrical shape and a driving end and an engaging end.

24. The adjustable spinal implant according to claim 23 wherein said engaging end of said cam further comprises a first curvate surface corresponding to an unlocked cam position and a second curvate surface corresponding to a locked cam position.

25. The adjustable spinal implant according to claim 24 wherein said cam is rotatable from said unlocked position to said locked position whereupon said rotation alternately moves said first curvate surface away from said rod and moves said second curvate surface into engagement with said rod through said rod opening.

26. The adjustable spinal implant according to claim 20 wherein said second fitting attached to said distal end of said housing is an articulating jaw engageable with a second rod.

27. The adjustable spinal implant according to claim 26 wherein said fixed jaw further comprises a proximal end and a distal end and an upper surface and a lower surface and a first side surface and a second side surface and a rod opening through said first and second side surfaces that is open at said lower surface, wherein said rod opening comprises a substantially cylindrical opening.

28. The adjustable spinal implant according to claim 27 wherein said fixed jaw further comprises an axial opening near said proximal end in open communication with said rod opening and a radial opening through said upper surface extending to said axial opening for receiving a locking device.

29. The adjustable spinal implant according to claim 28 wherein said locking device further comprises a cam having a generally cylindrical shape and a driving end and an engaging end.

30. The adjustable spinal implant according to claim 29 wherein said engaging end of said cam further comprises a first curvate surface corresponding to an unlocked cam position and a second curvate surface corresponding to a locked cam position.

31. The adjustable spinal implant according to claim 30 wherein said cam is rotatable from said unlocked position to said locked position whereupon said rotation alternately moves said first curvate surface away from said rod and moves said second curvate surface into engagement with said rod through said rod opening.

32. The adjustable spinal implant according to claim 20 wherein said first fitting attached to said distal end of said housing is a fixed jaw engageable with a second rod.

33. The adjustable spinal implant according to claim 32 wherein said fixed jaw further comprises a proximal end and a distal end and an upper surface and a lower surface and a first side surface and a second side surface and a rod opening through said first and second side surfaces that is open at said lower surface, wherein said rod opening comprises a substantially cylindrical opening.

34. The adjustable spinal implant according to claim 33 wherein said fixed jaw further comprises an axial opening near said proximal end in open communication with said rod opening and a radial opening through said upper surface extending to said axial opening for receiving a locking device.

35. The adjustable spinal implant according to claim 34 wherein said locking device further comprises a cam having a generally cylindrical shape and a driving end and an engaging end.

36. The adjustable spinal implant according to claim 35 wherein said engaging end of said cam further comprises a first curvate surface corresponding to an unlocked cam position and a second curvate surface corresponding to a locked cam position.

37. The adjustable spinal implant according to claim 36 wherein said cam is rotatable from said unlocked position to said locked position whereupon said rotation alternately moves said first curvate surface away from said rod and moves said second curvate surface into engagement with said rod through said rod opening.

38. The adjustable spinal implant according to claim 1 wherein said first fitting attached to said distal end of said extending shaft is a first articulating jaw and wherein said second fitting attached to said distal end of said housing is a second articulating jaw.

39. The adjustable spinal implant according to claim 38 wherein said first and second articulating jaws further comprise a proximal end and a distal end and an upper surface and a lower surface and a first side surface and a second side surface and a rod opening through said first and second side surfaces that is open at said lower surface, wherein said rod opening comprises a substantially cylindrical opening.

40. The adjustable spinal implant according to claim 39 wherein said first and second articulating jaws further comprise an axial opening near said proximal end in open communication with said rod opening and a radial opening through said upper surface extending to said axial opening for receiving a locking device.

41. The adjustable spinal implant according to claim 40 wherein said locking device further comprises a cam having a generally cylindrical shape and a driving end and an engaging end.

42. The adjustable spinal implant according to claim 41 wherein said engaging end of said cam further comprises a first curvate surface corresponding to an unlocked cam position and a second curvate surface corresponding to a locked cam position.

43. The adjustable spinal implant according to claim 42 wherein said cam is rotatable from said unlocked position to said locked position whereupon said rotation alternately moves said first curvate surface away from said rod and moves said second curvate surface into engagement with said rod through said axial opening.

44. The adjustable spinal implant according to claim 1 wherein said second fitting attached to said distal end of said housing further comprises an articulating jaw engageable with a second rod.

45. The adjustable spinal implant according to claim 44 wherein said articulating jaw further comprises a proximal end and a distal end and an upper surface and a lower surface and a first side surface and a second side surface and a rod opening through said first and second side surfaces that is open at said lower surface, wherein said rod opening comprises a substantially cylindrical opening.

46. The adjustable spinal implant according to claim 45 wherein said articulating jaw further comprises an axial opening near said proximal end in open communication with said rod opening and a radial opening through said upper surface extending to said axial opening for receiving a locking device.

47. The adjustable spinal implant according to claim 46 wherein said locking device further comprises a cam having a generally cylindrical shape and a driving end and an engaging end.

48. The adjustable spinal implant according to claim 47 wherein said engaging end of said cam further comprises a first curvate surface corresponding to an unlocked cam position and a second curvate surface corresponding to a locked cam position.

49. The adjustable spinal implant according to claim 48 wherein said cam is rotatable from said unlocked position to said locked position whereupon said rotation alternately moves said first curvate surface away from said rod and moves said second curvate surface into engagement with said rod through said axial opening.

50. The adjustable spinal implant according to claim 3 wherein said outer surface of said rotor further comprises a taper thereon.

51. The adjustable spinal implant according to claim 50 wherein said inner surface of said locking collar further comprises a taper thereon engageable with said taper on said outer surface of said rotor.

52. An adjustable spinal implant comprising:
- an extending shaft having a proximal end and a distal end and having one or more helical grooves disposed on an external surface of said extending shaft;
- a fixed jaw attached to said distal end of said extending shaft for engaging a rod, said fixed jaw further comprising a proximal end and a distal end and an upper surface and a lower surface and a first side surface and a second side surface; a rod opening through said first and second side surfaces and open at said lower surface; an axial opening near said proximal end and in open communication with said rod opening; and a radial opening through said upper surface extending to said axial opening;
- a substantially cylindrical housing having a proximal end and a distal end and an inner surface and an outer surface, wherein said proximal end of said housing receives therewithin said proximal end of said extending shaft and wherein said distal end further comprises a socket therewithin;
- a substantially cylindrical rotor having an outer surface with circumferential grooves thereon and an inner surface with one or more helical grooves thereon wherein said one or more helical grooves are engageable with said one or more helical grooves on said extending shaft, wherein said rotor is axially fixed with respect to said housing;
- a locking collar disposed about said outer surface of said housing at said proximal end of said housing, wherein said locking collar is substantially cylindrical in shape and comprises an outer surface and an inner surface and at least one protrusion directed radially inwardly for engagement with said circumferential grooves of outer surface of said substantially cylindrical rotor; and
- an articulating jaw attached to said distal end of said housing for engaging a rod, said articulating jaw further comprising a proximal end and a distal end and an upper surface and a lower surface and a first side surface and a second side surface; a rod opening through said first and second side surfaces and open at said lower surface; an axial opening near said proximal end; and a radial opening through said upper surface extending to said axial opening; and a ball depending from said proximal end for engagement in said socket of said housing; and
- a locking cam disposed within each said radial opening of said fixed jaw and said articulating jaw further comprising a generally cylindrical member having a driving end and an engaging end wherein said engaging end comprises a first concave curvate surface corresponding to an unlocked position and a second concave curvate surface corresponding to a locked position;
- wherein said extending shaft is moveable within said proximal end of said housing and as said shaft moves, said helical grooves thereon engage said helical grooves of said rotor, causing said rotor to spin and wherein sliding said locking collar from said unlocked position to said locked position moves said one or more protrusions into engagement with said circumferential grooves, thus fixing the length of said implant; and wherein rotating said locking cam from said unlocked position to said locked position brings said second concave curvate surface into contact with said rod, locking said rod to said implant.

53. An adjustable spinal implant comprising:
- an extending shaft having a proximal end and a distal end and having one or more helical grooves disposed on an external surface of said extending shaft;
- a first articulating jaw attached to said distal end of said extending shaft for engaging a rod, said fixed jaw further comprising a proximal end and a distal end and an upper surface and a lower surface and a first side surface and a second side surface; a rod opening through said first and second side surfaces and open at said lower surface; an axial opening near said proximal end and in open communication with said rod opening; and a radial opening through said upper surface extending to said axial opening;
- a substantially cylindrical housing having a proximal end and a distal end and an inner surface and an outer surface, wherein said proximal end of said housing receives therewithin said proximal end of said extending shaft and wherein said distal end further comprises a socket therewithin;
- a substantially cylindrical rotor having an outer surface with circumferential grooves thereon and an inner surface with one or more helical grooves thereon wherein said one or more helical grooves are engageable with said one or more helical grooves on said extending shaft, wherein said rotor is axially fixed with respect to said housing;
- a locking collar disposed about said outer surface of said housing at said proximal end of said housing, wherein said locking collar is substantially cylindrical in shape and comprises an outer surface and an inner surface and at least one protrusion directed radially inwardly for engagement with said circumferential grooves of outer surface of said substantially cylindrical rotor; and
- a second articulating jaw attached to said distal end of said housing for engaging a rod, said articulating jaw further comprising a proximal end and a distal end and an upper surface and a lower surface and a first side surface and a second side surface; a rod opening through said first and second side surfaces and open at said lower surface; an axial opening near said proximal end; and a radial opening through said upper surface extending to said axial opening; and a ball depending from said proximal end for engagement in said socket of said housing; and
- a locking cam disposed within each said radial opening of said first and second articulating jaws further comprising a generally cylindrical member having a driving end and an engaging end wherein said engaging end comprises a first concave curvate surface corresponding to an unlocked position and a second concave curvate surface corresponding to a locked position;
- wherein said extending shaft is moveable within said proximal end of said housing and as said shaft moves therewithin, said helical grooves thereon engage said helical grooves of said rotor, causing said rotor to spin and wherein sliding said locking collar from said unlocked position to said locked position moves said one or more protrusions into engagement with said circumferential grooves, thus fixing the length of said implant; and wherein rotating said locking cam from said unlocked position to said locked position brings said second concave curvate surface into contact with said rod, locking said rod to said implant.

54. An adjustable spinal implant comprising:
- a substantially cylindrical housing having a proximal end and a distal end and having an axial opening therein;
- an extending shaft having a proximal end and a distal end wherein said proximal end is insertable into said axial opening;
- a rotor rotatably disposed within said axial opening and having an external surface and an internal surface wherein said internal surface engagingly cooperates with said extending shaft, wherein said rotor is axially fixed with respect to said housing;

a locking collar disposed on said substantially cylindrical housing slideable between an unlocked position wherein said locking collar does not engage said rotor and a locked position wherein said locking collar engages said rotor;

a first fitting attached to said distal end of said extending shaft; and a second fitting attached to said distal end of said substantially cylindrical housing.

55. The adjustable spinal implant according to claim 1 wherein translational motion of said extending shaft relative to said housing causes rotational motion of said rotor with respect to said housing.

56. The adjustable spinal implant according to claim 52 wherein translational motion of said extending shaft relative to said housing causes rotational motion of said rotor with respect to said housing.

57. The adjustable spinal implant according to claim 53 wherein translational motion of said extending shaft relative to said housing causes rotational motion of said rotor with respect to said housing.

58. The adjustable spinal implant according to claim 54 wherein translational motion of said extending shaft relative to said housing causes rotational motion of said rotor with respect to said housing.

* * * * *